United States Patent
Coy

(10) Patent No.: US 11,236,381 B2
(45) Date of Patent: Feb. 1, 2022

(54) METHOD FOR CHECKING AND CONTROLLING THE MAMMALIAN LACTIC ACID FERMENTATION PROCESS/AEROBIC GLUCOSE FERMENTATION METABOLIC PATHWAY IN MAMMALIAN ORGANISM

(76) Inventor: Johannes Coy, Otzberg (DE)

(*) Notice: Subject to any disclaimer, the term of this patent is extended or adjusted under 35 U.S.C. 154(b) by 2503 days.

(21) Appl. No.: 12/790,257

(22) Filed: May 28, 2010

(65) Prior Publication Data

US 2010/0240687 A1 Sep. 23, 2010

Related U.S. Application Data

(62) Division of application No. 11/571,205, filed as application No. PCT/EP2006/001951 on Mar. 3, 2006, now Pat. No. 7,754,437.

(30) Foreign Application Priority Data

| Mar. 7, 2005 | (EP) | 05004930 |
| Jun. 17, 2005 | (EP) | 05013170 |

(51) Int. Cl.
| C12Q 1/54 | (2006.01) |
| C12Q 1/48 | (2006.01) |
| C12Q 1/30 | (2006.01) |
| G01N 1/30 | (2006.01) |

(52) U.S. Cl.
CPC .......... *C12Q 1/54* (2013.01); *C12Q 1/48* (2013.01); *G01N 1/30* (2013.01)

(58) Field of Classification Search
CPC .. A61P 17/02; A61P 19/02; A61P 1/04; A61P 21/00; A61P 25/00; A61P 25/28; A61P 29/00; A61P 37/02; A61P 37/06; A61P 3/04; A61P 3/06; A61P 3/08; A61P 3/10; A61P 43/00; A61P 9/10; C12Q 1/48; C12Q 1/54; G01N 1/30; G01N 2333/9104; G01N 33/6893; G01N 33/6896
See application file for complete search history.

(56) References Cited

U.S. PATENT DOCUMENTS

2003/0113329 A1* 6/2003 Ramakrishnan ........... 424/146.1

FOREIGN PATENT DOCUMENTS

| EP | 1354961 A1 | 10/2003 |
| WO | 03089667 A1 | 10/2003 |

OTHER PUBLICATIONS

Anjaneyulu et al., Quercetin, an Anti-Oxidant Bioflavonoid, Attenuates Diabetic Nephropathy in Rats, 2004, Clinical and Experimental Pharmacology and physiology, 31: 244-248.*
Hammes et al., Benfotiamine blocks three major pathways of hyperglycemic damage and prevents experimental diabetic retinopathy, 2003, Nature Medicine, 9: 294-299.*
Stracke et al., A Benfotiamine-vitamin B combination in treatment of diabetic polyneuropathy, 1996, Exp Clin Endocrinol Diabetes, 104: 311-316.*
Human Protein Atlas, 2017 http://www.proteinatlas.org/ENSG00000007350-TKTL1/cancer.*
2007, http://www.lifeextension.com/Magazine/2007/1/report_benfotiamine/Page-01.*
Coy et al.: "Mutations in teh Transketolase-Like Gne TKTL1: Clinical Implications for Neurodegenerative Diseases, Diabetes adn Cancer," in Clinical Laboratory, Clin Lab Publications, Heidelberg, DE, vol. 51, No. 5/6, 2005, pp. 257-273.
Hammes et al.: "Benfotiamine Blocks Three Major Pathways of Hyperglycemic Damage and Prevents Experimental Diabetic Retinopathy," in Nature Medicine, Nature Publishing Group, New York, NY, US, vol. 9, No. 3, Mar. 2003, pp. 294-299.
Kaaks et al. : "Nutrient Intake Patterns and Gastric Cancer Risk: a Case-Control Study in Belgium" in Int. J. Cancer: 78, pp. 415-420, 1998.
Coy et al.: "Mutations in The Transketolase-Like GNE TKTL1: Clinical Implications for Neurodegenerative Diseases, Diabetes and Cancer," in Clinical Laboratory, Clin Lab Publications, Heidelberg, DE, vol. 51, No. 5/6, 2005, pp. 257-273.
Hammes et al.: "Benfotiamine Blocks Three Major Pathways of Hyperglycemic Damage and Prevents Experimental Diabetic Retinopathy," in Nature Medicine, Nature Publishing Group, New York, NY, US, vol. 9, No. 3, 2003-03, pp. 294-299.
Bloedon et al., "Safety and Pharmacokinetics of Purified Soy Isoflavones: Single-Dose Administration To Postmenopausal Women," in The American Journal of Clinical Nutrition, Nov. 2002, vol. 76, No. 5, pp. 1126-1137.

* cited by examiner

*Primary Examiner* — Aaron J Kosar
(74) *Attorney, Agent, or Firm* — Agris & von Natzmer, LLP; Joyce v. Natzmer

(57) ABSTRACT

The method for qualitative and quantitative detecting of the extend of use and the correct process flow of the mammalian aerobic glucose fermentation metabolic pathway (mam-aGF) in a mammalian individual is characterized in that the enzyme TKTL1 is used as indicator and target molecule and the structural and/or functional parameter of said TKTL1 in a biological sample of said individual (patient) are taken as indication for the qualitative and quantitative run of the mam-aGF in the cells and/or tissue of said individual (patient). In combination with the use of inhibitors and activators of the mam-aGF the method is further suitable for checking and controlling the mam-aGF in an individual (patient).

6 Claims, 17 Drawing Sheets

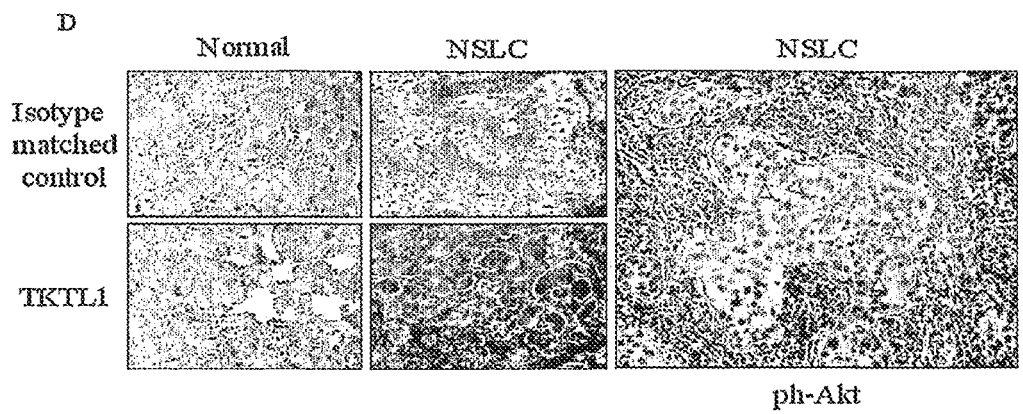
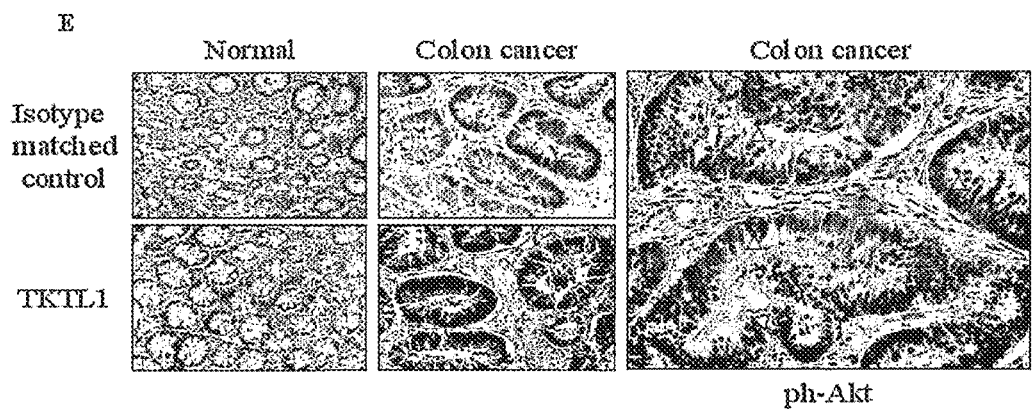
Fig.7

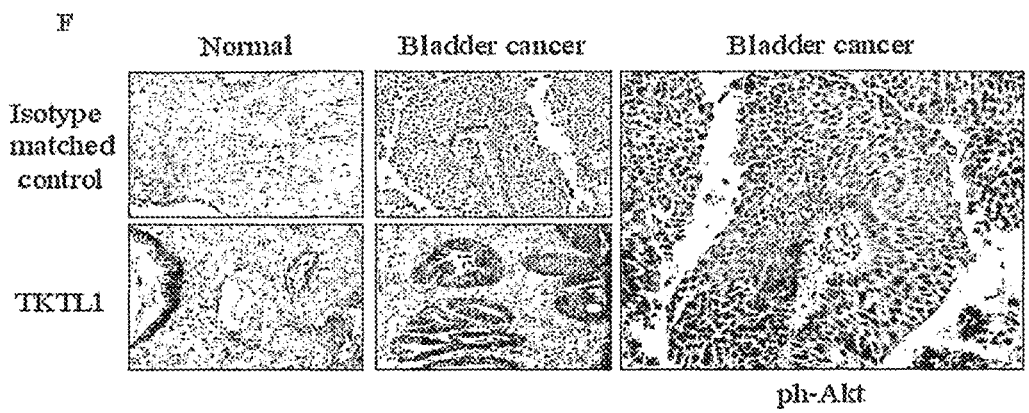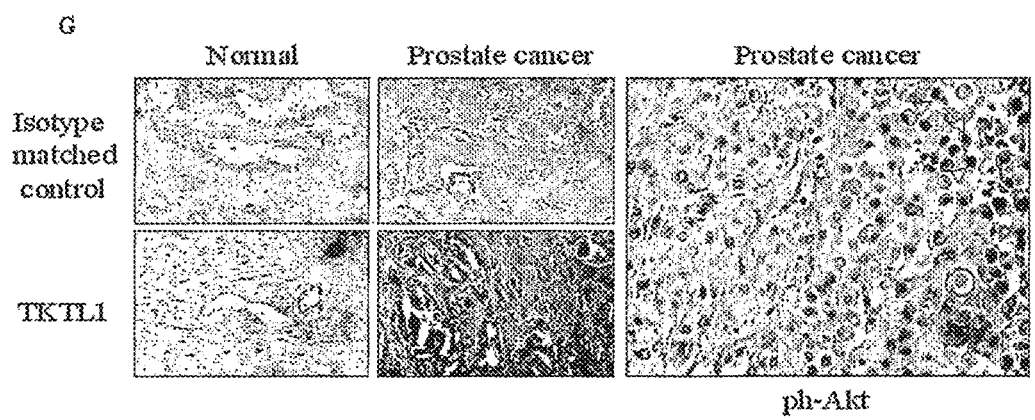
Fig.8

Fig. 9 TKTL1 expression in endothelium

TKTL1 expression in nerve 2D-gel electrophoresis of TKTL1 multi-protein complex

A

|   | 1 | 2 | 3 | 4 | 5 | 6 | 7 | 8 | 9 | 10 | 11 | 12 |
|---|---|---|---|---|---|---|---|---|---|----|----|----|
| A | 0.034 | 0.037 | 0.030 | 0.039 | 0.036 | 0.055 | 0.043 | 0.047 | 0.041 | 0.051 | 0.014 | 0.017 |
| B | 0.043 | 0.036 | 0.039 | 0.044 | 0.034 | 0.048 | 0.039 | 0.037 | 0.043 | 0.036 | 0.017 | 0.015 |
| C | 0.893 | 0.699 | 0.124 | 0.937 | 0.860 | 0.146 | 0.119 | 0.723 | 0.493 | 0.169 | 0.926 | 0.791 |
| D | 1.169 | 1.805 | 1.703 | 0.790 | 0.039 | 1.047 | 1.389 | 0.420 | 1.533 | 0.258 | 0.303 | 1.539 |
| E | 1.422 | 1.890 | 0.903 | 1.629 | 1.380 | 1.307 | 0.477 | 1.408 | 1.408 | 1.045 | 1.243 | 1.368 |
| F | 0.911 | 0.576 | 1.380 | 2.158 | 0.701 | 1.043 | 1.344 | 0.289 | 1.206 | 1.638 | 2.018 | 1.454 |
| G | 1.257 | 1.450 | 0.799 | 1.489 | 1.257 | 1.057 | 1.346 | 0.892 | 0.701 | 1.924 | 1.630 | 1.835 |
| H | 1.530 | 0.803 | 1.322 | 0.519 | 0.506 | 1.503 | 1.256 | 0.493 | 0.820 | 0.913 | 1.772 | 1.134 |

B

|   | 1 | 2 | 3 | 4 | 5 | 6 | 7 | 8 | 9 | 10 | 11 | 12 |
|---|---|---|---|---|---|---|---|---|---|----|----|----|
| A | 2.018 | 1.935 | 1.804 | 1.409 | 2.085 | 1.930 | 1.460 | 2.103 | 1.864 | 1.709 | 0.037 | 0.042 |
| B | 1.480 | 1.993 | 1.635 | 1.993 | 1.920 | 1.488 | 1.703 | 1.939 | 1.794 | 1.504 | 0.036 | 0.039 |
| C | 1.593 | 1.429 | 1.500 | 1.703 | 1.229 | 1.593 | 1.559 | 1.703 | 1.550 | 1.838 | 1.993 | 1.504 |
| D | 0.273 | 0.493 | 0.380 | 0.180 | 0.320 | 0.228 | 0.219 | 0.302 | 0.320 | 0.250 | 0.183 | 0.249 |
| E | 0.239 | 0.396 | 0.320 | 0.370 | 0.329 | 0.264 | 0.270 | 0.320 | 0.401 | 0.222 | 0.199 | 0.243 |
| F | 0.410 | 0.399 | 0.370 | 0.323 | 0.305 | 0.299 | 0.378 | 0.322 | 0.399 | 0.461 | 0.295 | 0.348 |
| G | 0.281 | 0.310 | 0.352 | 0.383 | 0.356 | 0.328 | 0.344 | 0.325 | 0.294 | 0.274 | 0.287 | 0.259 |
| H | 0.193 | 0.190 | 0.218 | 0.301 | 0.317 | 0.170 | 0.194 | 0.253 | 0.199 | 0.207 | 0.242 | 0.322 |

A - Determination of TKTL1 protein isoforms by ELISA
B - transketolase activity of isolated TKTL1 protein

Fig. 17

METHOD FOR CHECKING AND CONTROLLING THE MAMMALIAN LACTIC ACID FERMENTATION PROCESS/AEROBIC GLUCOSE FERMENTATION METABOLIC PATHWAY IN MAMMALIAN ORGANISM

This is a divisional application claiming benefit of U.S. application Ser. No. 11/571,205 filed Dec. 22, 2006, which is incorporated herein by reference in its entirety and which is U.S. national stage of International application no. PCT/EP2006/001951, filed Mar. 3, 2006 designating the United States and which claims priority to European application no. EP 05 004 930.3, filed Mar. 7, 2005 and to European application no. EP 05 013 170.5, filed Jun. 17, 2005.

The invention relates to (1) a method for qualitative and quantitative detection of the mammalian lactic acid fermentation process or mammalian aerobic glucose fermentation metabolic pathway, respectively, in a mammalian individual (patient, mammalian organism), (2) a method for checking and controlling (i.e. inhibiting or activating) said process/pathway, and (3) inhibitors and activators of that process/pathway.

The invention is based on the novel scientific discovery, that (1) a metabolism pathway which up to now has been known only from prokaryotic cells (for example from *lactobacillus*), exists in mammalian organisms—i.e. in mammalian cells—too, said metabolism pathway comprising the energy-yielding breaking down of glucose to lactate, although sufficient free (molecular) oxygen is present and bioavailable i.e. aerobic conditions exist, and that (2) the enzyme TKTL1 is the tracer enzyme of said new glucose fermentation metabolism.

Mammalian cells are able to break down glucose to lactic acid in the case of oxygen deficiency, finally leading to muscles ache. This anaerobic glucose degradation is performed via the Embden-Meyerhof-pathway. In the 1920s Otto Warburg discovered that also in the presence of sufficient available amounts of oxygen mammalian cells are able to break down glucose to lactic acid, i.e. that mammalian cells are able to ferment glucose to lactic acid even in the presence of sufficient amounts of free bioavailable oxygen. He observed this anaerobic glucose to lactate degradation pathway in the presence of oxygen in tumor tissues as well as in certain healthy tissues like retina and testis. For historical reasons this glucose degradation to lactate even in the presence of oxygen is named aerobic glycolysis or Warburg effect. Since the start and end point (glucose and lactate) is the same as the glucose fermentation to lactate in the absence of oxygen via the Embden-Meyerhof pathway, the lactate production has been interpreted as the result of the Embden-Meyerhof pathway. However, in the course of the experiments leading to the present invention it became obvious that it is the TKTL1 transketolase which allows the glucose degradation or glucose fermentation, respectively, to lactate even in the presence of oxygen and that this glucose pathway is significantly different from the Embden-Meyerhof pathway.

The TKTL1 transketolase gene has been discovered some years ago, namely 1996 by Coy et al. (Genomics 32, 309-316). Due to a stop codon in a predicted coding exon, the TKTL1 transketolase gene has been annotated as a pseudogene in sequence data bases. Despite this, in 2002 Coy demonstrated that the TKTL1 gene encodes an enzymatically active transketolase. The TKTL1 transketolase is phylogenetically cognate with the two other known human transketolases TKT and TKTL2. However, all three transketolase enzymes are encoded by different genes, whereby the gene for TKT is located on chromosome 3, the gene for TKTL2 is located on chromosome 4 and the gene for TKTL1 is located in band Xq28 on chromosome X. in humans.

One most important function of the enzyme TKTL1 in mammalian cells is its catalysator function during the fermentation of glucose to lactic acid in the presence of oxygen, i.e. under aerobic conditions. TKTL1 is the tracer enzyme in the novel, first recently discovered so called mammalian aerobic glucose fermentation metabolic pathway or mammalian lactic acid fermentation process, respectively. In the following this newly discovered pathway is referred to as mammalian aerobic glucose fermentation metabolic pathway or shortened to mam-aGF, respectively.

Details of that mam-aGF are the following:

A protein complex containing TKTL1 and glyceraldehyd-3-phosphate dehydrogenase (GAPD) allows a nonoxidative glucose degradation. The electron transfer does not involve mitochondria and allows a mitochondria independent ATP production in TKTL1 expressing cells. Application of anti-TKTL1 compounds, or inhibitory thiamin-analogs, or para-benzoquinons (or benzoquinone-derivatives) can be applied for the inhibition of such a mitochondria independent ATP production (in particular for example in tumors with a TKTL1 based sugar metabolism).

Using the human TKTL1 protein the inventor of the present patent application confirmed the formation of glyceraldehyd-3-phosphate in an one-substrate reaction utilizing X5P as sole carbon source.

The metabolism of X5P via TKTL1 result in the formation of acetyl-CoA. The anaerobic glucose degradation under aerobic conditions leads to lactate and the building of the energy rich compound acetyl-CoA. The pyruvate dehydrogenase complex is then e.g. inhibited by acetyl-CoA, and as a consequence, pyruvate is mainly reduced to lactate.

A schematic description of the complete mam-aGF are given in FIG. 13 and FIG. 14.

Details concerning the tracer enzyme TKTL1 of that mam-aGF are the following:

During the experiments leading to the present invention different TKTL1 isoforms were identified on protein level using a novel monoclonal antibody (Linaris Biologische Produkte GmbH, Wertheim) specifically detecting the TKTL1 protein.

TKTL1 protein isoforms are part of a multi-protein complex. Within this complex TKTL1 is also bound to transketolase unrelated proteins like glyceraldehyd-3-phosphate dehydrogenase (GAPDH), DNaseX (DNase1-like-1), Akt (=protein kinase B); histones, histon deacetylase, amyloid precursor protein and actin binding proteins.

Known transketolases are homodimers of two full length proteins harbouring all typical invariant transketolase amino acid residues. The transketolase-like gene encoded TKTL1 protein isoforms build TKTL1 homo/heterodimers and TKT/TKTL1 or TKTL2/TKTL1 heterodimers. The expression of TKTL1 protein isoforms—even an enzymatically non-active isoform—influences the enzymatic activity of a TKT or TKTL2 protein as part of a TKT/TKTL1 or TKTL2/TKTL1 heterodimer. A molecular switch and a proton wire synchronize the active sites in TKT/TKTL1, TKTL2/TKTL1 and TKTL1/TKTL1 homo- and heterodimers.

The proof that the TKTL1 gene (NM_012253; Accession Numbers: X91817; BC025382) encodes a full length transketolase protein as well as smaller protein isoforms has important implications for basic research and medical health.

Besides their enzymatic functions, the TKTL1 proteins exhibit various different functions depending on the localization of the proteins in the mammalian cell and on their state of aggregation. In mammalian cells the TKTL1 protein is mainly located in the cytoplasm, but also occurs in the nucleus. Within the cytoplasm the main function of TKTL1 is the catalysis of the (trans-)ketolase reaction. Additional functions of the TKTL1 proteins located within the nucleus are associated with the control of the cell cycle and mitosis, control of transcription (the TKTL1 gene itself and others), and regulation of apoptosis.

The TKTL1 proteins (with their functions depending on their localization or the state of aggregation) are designated as "moonlighting" proteins, since they execute different functions depending on subcellular localization, the cell type as well as its aggregation state.

The present invention is based on the object (a) of making available a method for a qualitative and quantitative detecting (and monitoring) of the extend (level) of use and the correct (normal, natural) process flow of the mammalian aerobic glucose fermentation metabolic pathway (mam-aGF) in a mammalian individual, i.e. a method for controlling whether that metabolism/pathway/process actually proceeds in the investigated cells of the appropriate mammalian organism, if the case is given in what extend and whether it proceeds "normal" or correct, respectively or with faults or aberrations, and (b) of making available a means with which that mam-aGF can be affected, in particular enhanced or inhibited.

This object is achieved with a (in-vitro-) method for the qualitative and quantitative detecting (and monitoring) the extend (level) of use and the correct (normal, natural) process flow of the eukaryotic aerobic glucose fermentation metabolic pathway "mam-aGF" (or mammalian lactic acid fermentation process) in a mammalian individual (patient), characterized in that (a) the enzyme TKTL1 is used as indicator and target molecule and (b) said method comprises the following steps:
  taking (harvesting, collecting) a biological sample of said individual (patient),
  determining the activity and/or concentration, and/or cellular localization and/or aggregation status and/or dimerization status of the TKTL1 protein within said sample of said individual (patient) and within a control sample,
  comparing the determined data obtained from said sample of said individual (patient) with the data obtained from the control sample,
  and taking (i) an enhanced or decreased level of activity and/or concentration of the TKTL1 protein in said sample of the individual compared to the control sample as indication of an enhanced or decreased, respectively, extend (level) of use of the mammalian aerobic glucose fermentation metabolic pathway "mam-aGF",
and (ii) an abnormal cellular localization and/or an abnormal aggregation status and/or an abnormal dimerization status of the TKTL1 protein in said sample of the individual compared to the control sample as indication of an abnormal (defective, disturbed, faulty) mammalian aerobic glucose fermentation metabolic pathway.

The detection (determination) may be carried out in solution or using reagents fixed to a solid phase. The detection of one or more molecular markers, such as polypeptides or nucleic acids, may be performed in a single reaction mixture or in two or separate reaction mixtures. Alternatively, the detection reactions for several marker molecules may, for example, be performed simultaneously in multi-well reaction vessels. The markers characteristic for the TKTL1 gene products may be detected using reagents that specifically recognize these molecules. The detection reaction for the marker molecules may comprise one or more reactions with detecting agents either recognizing the initial marker molecules or recognizing the prior molecules used to recognize other molecules.

The detection reaction further may comprise a reporter reaction indicating the presence or absence and/or the level of the TKTL1 gene markers. The reporter reaction may be for example a reaction producing a coloured compound, a bioluminescence reaction, a fluorescence reaction, generally a radiation emitting reaction etc. In a preferred embodiment, different marker molecules may be recognized by agents that produce different reporter signals, so that the signals referring to marker molecules could be distinguished.

Applicable formats for the detection reaction according to the present invention may be, blotting techniques, such as Western-Blot, Southern-blot, and Northern-blot. The blotting techniques are known to those of ordinary skilled in the art and may be performed for example as electro-blots, semidry-blots, vacuum-blots or dot-blots. Amplification reactions may also be applicable for the detection of e.g. nucleic acid molecules. Furthermore immunological methods for detection of molecules may be applied, such as for example immunoprecipitation or immunological assays, such as ELISA, RIA, lateral flow assays, immuno-cyto-chemical methods etc.

On the basis of the information obtained with that method a medical practitioner is able to draw conclusions concerning the state of health of the appropriate individual (patient) and to evolve schedules for therapy if necessary.

Therefore said method is suitable and intended for monitoring (detecting, surveying and observing) the course of diseases, associated with an increased or decreased and/or abnormal, i.e. defective/faulty/disturbed mam-aGF.

The determination of TKTL1 activity and/or concentration may comprise determining the level of TKTL1 gene products or determining the enzymatic activity of TKTL1 in a sample.

Monitoring may comprise detecting the level of TKTL1 gene products or TKTL1 enzymatic activity in samples taken at different points in time and determining the changes in said level. According to said changes the course of the disease can be followed. The course of the disease may be used to select therapy strategies for the particular individual.

Another aspect of detecting and monitoring of the disease course may comprise the detection of minimal residual disease. This may comprise for example the detection of a TKTL1 gene products level or TKTL1 enzymatic activity in one or more body samples following initial therapy of an individual once or at several time points. According to the level of TKTL1 gene products detected in the samples one may select a suitable therapy for the particular individual.

Based upon the determined level of TKTL1 gene products or the determined enzymatic activity in the samples individuals can be subdivided into subgroups. Based upon these subgroups an assessment of prognosis may be done. According to the subgroups the therapy of the individuals affected by the various diseases may be tailored. For example the overexpression of TKTL1 gene and an enhanced activity of the pentose-phosphate cycle suggest a mechanism by which thiamine (vitamin B1) promotes nucleic acid ribose synthesis and an enhanced glucose metabolism. Therefore the thiamine intake has direct consequences for a disease with an overexpression of the transketolase like-1 gene. This provides also background information and helps to develop guidelines for alternative treatments with antithiamine transketolase inhibitors in the clinical setting. Analysis of RNA ribose indicates that glucose carbons contribute to over 90% of ribose synthesis in cultured cervix and pancreatic carcinoma cells and that ribose is synthesized primarily through the thiamine dependent transketolase pathway (>70%). Antithiamine compounds significantly inhibit nucleic acid synthesis. Thiamine or benfotiamine treatment activates TKTL1 and thereby the sugar metabolism and reduces toxic or unwanted reactions (e.g. AGE formation, glyoxal.

In addition said method may comprise the detection of auto-antibodies directed against polypeptides encoded by the TKTL1 gene. The polypeptides used for the methods according to the present invention may be used to detect the presence or absence of such antibodies in body fluids by methods known to those of skill in the art.

Said method is further suitable for performing an in-vivo or in-vitro molecular imaging so that it is possible to identify diseases associated with an increased or decreased or abnormal i.e. defective mam-aGF in a very early stage, ideally before the appearance of the typically known symptoms of that disease. In consequence the individual or its doctor is able to medicate that disease at a very early point of time thereby significantly increasing the chances of healing.

Molecular imaging differs from conventional techniques because it identifies specific gene products and intracellular processes like specific enzyme reactions. The altered substrate specificity and reaction modus of the TKTL1 enzyme can be used for the detection of cells or tissues with an enhanced or reduced TKTL1 enzyme activity. The altered substrate specificity and reaction modus of the TKTL1 enzyme allows the discrimination between the enzymatic activity of three transketolase(-like) enzymes thereby allowing the measurement of TKTL1 enzymatic activity in vivo. The enzymatic activity can be detected by e.g. positron emission tomography, chemoluminescence or radiographic imaging.

The molecular imaging may be based on the enzymatic conversion of inert or labelled compounds to molecules detectable in the course of molecular imaging methods by the TKTL1 molecules. In another embodiment the molecular imaging method may be based on the use of compounds carrying a suitable label for in vivo molecular imaging, such as radio isotopes, metal ions etc., specifically binding to TKTL1 molecules in vivo.

These compounds are preferably non-toxic and may be eliminated from the circulation of organisms, such as humans, in a time span, that allows for performing the detection of label accumulated in tissue overexpressing TKTL1 gene. In cases of a molecular imaging, for which clearance from the circulation is not relevant (for example due to low background produced by the circulating molecules etc.) the compounds for use should be administered in pharmaceutical acceptable form in compositions that may additionally comprise any other suitable substances, such as e.g. other diagnostically useful substances, therapeutically useful substances, carrier substances or the like.

The biological sample of the individual can be almost each tissue or liquid sample obtained from said individual. Isolated cells, lysed cells, cell debris, peptides or nucleic acids of said individual are suitable samples, too. Further suitable samples are for example biopsy preparations, body fluids, secretions, a smear, serum, urine, semen, stool, bile, a liquid containing cells.

The determination in step (b) of the inventive method can be carried out on the protein level, i.e. with the TKTL1 protein or a TKTL1 protein fragment as the target. Preferably the determination is carried out by using a molecule that specifically binds to the TKTL1 protein.

Preferably said molecule is an antibody directed to TKTL1 or a fragment of such anti-TKTL1-antibody or a peptidomimetic comprising an antigen binding epitope, or a mini-antibody.

Suitable target molecules are the TKTL1 protein itself or fragment thereof or a fusion protein comprising the TKTL1 protein.

The determination on the protein level, i.e. of the TKTL1 gene products, can for example be carried out in a reaction comprising an antibody specific for the detection of the TKTL1 protein. The antibodies can be used in many different detection techniques for example in Western-blot, ELISA or immunoprecipitation. Generally antibody based detection can be carried out as well in vitro as directly in situ for example in the course of an immuno-histochemical staining reaction. Any other method for determining the amount of particular polypeptides in biological samples can be used according to the present invention.

The reagent for the detection of the TKTL1 gene product may include any agent capable of binding to the TKTL1 protein molecule. Such reagents may include proteins, polypeptides, nucleic acids, peptide nucleic acids, glycoproteins, proteoglycans, polysaccharides or lipids.

TKTL1 gene products as used in the context of the present invention may comprise polypeptides and nucleic acids encoded by the transketolase like-1 gene. The polypeptides and polynucleotides (cf. TKTL1, TKR: NM_012253; Accession numbers: X91817; BC025382) used for performing the method according to the present invention are isolated. This means that the molecules are removed from their original environment. Naturally occurring proteins are isolated if they are separated from some or all of the materials, which coexist in the natural environment. Polynucleotides are isolated for example if they are cloned into vectors.

In addition to TKTL1 protein variants with enhanced or reduced levels of enzymatic activity, TKTL1 proteins with altered localization or aggregation and/or dimerization within the cell can be detected in patients. Using monoclonal antibodies specifically detecting TKTL1 protein (Linaris Biologische Produkte, Wertheim) TKTL1 protein within the nucleus can be detected in cells isolated from body fluids. Using immunocytochemistry the localization of TKTL1 within the nucleus and the cytoplasm of cells from healthy individuals and patients can be determined. In a subset of Alzheimer patients an enhanced localization of TKTL1 is detectable within the nucleus. A different aggregation of TKTL1 in Alzheimer patients is also present. Detection of this aggregation is possible using 2D-gel electrophoresis (FIG. 15). In addition an aggregation with other proteins e.g. GAPDH can be detected by an ELISA using antibodies for TKTL1 and GAPDH.

Just as well the determination in step (b) of the inventive method can be carried out on the nucleic acid level, i.e. with the TKTL1 nucleic acid or a fragment thereof as the target. The term "TKTL1 nucleic acid" as used in the present context comprises the TKTL1 gene, TKTL1 mRNAs and TKTL1 encoding nucleic acids.

In a preferred embodiment the detection of the above mentioned relevant TKTL1 parameter in the sample should be performed by using at least one nucleic acid probe capable of hybridizing to a TKTL1 nucleic acid. A suitable target molecule is the TKTL1 nucleic acid itself as well as a chimeric nucleic acid comprising a TKTL1 encoding nucleic acid or fragments thereof.

The procedure for the detection of nucleic acids (DNA and/or RNA) can, for example, be carried out by a binding reaction of the molecule to be detected to complementary nucleic acid probes, proteins with binding specificity for the nucleic acids or any other entities specifically recognizing and binding to said nucleic acids. This method can be performed as well in vitro as directly in situ for example in the course of a detecting staining reaction. Another way of detecting the TKTL1 gene products in a sample on the level of nucleic acids performed in the method according to the present invention is an amplification reaction of nucleic acids, which can be carried out in a quantitative manner such as for example the polymerase chain reaction. In a preferred embodiment of the present invention real time RT PCR may be used to quantify the level of TKTL1 RNA in samples.

The TKTL1 sample for carrying out a positive control may comprise for example TKTL1 nucleic acids or polypeptides or fragments thereof in applicable form, such as solution or salt, peptides in applicable form, tissue section samples or positive cells.

In summary: the type (manner) of TKTL1 enzyme activity (normal, reduced or enhanced) can be identified in individuals based on TKTL1 gene mutations, reduced or enhanced enzyme activities of the isolated TKTL1 protein or an in vivo imaging of the TKTL1 enzyme reaction. Diagnosis can be performed by determining the enzymatic activity of the TKTL1 protein isolated from the patient (e.g. serum, liquor, or other body fluids) or by in vivo imaging of TKTL1 enzyme activity.

Kits for performing the inventive method can contain diagnostic systems that rely on bioluminescence for visualizing tissues in situ. These systems can further include compositions containing substrates that are converted by the TKTL1 enzymatic activity. In particular these systems can include a composition that contains a bioluminescence generating reaction. Administration of the compositions results in production of light by targeted tissues that permits the detection and localization of cells or tissues e.g. for surgical removal.

For performing the inventive method in course of a molecular imaging, in particular a radiographic imaging of tissue, it is proposed to use a radio-opaque imaging agent that in one embodiment accumulates intracellular in tissue in proportion to its functional, or physiological, activity. In one embodiment, the imaging agent is a cell membrane-permeable, radio-opaque, selective substrate or high affinity ligand for TKTL1.

The present invention therefore also relates to labeled TKTL1 substrates and the use of same as imaging agents, for example as positron emission tomography (PET) imaging agents or magnetic resonance thomography (MRT) imaging agents for the noninvasive detection and localization of cells and tissues with an enhanced or reduced TKTL1 enzymatic activity.

A very suitable labelled substrate for use as imaging agents for PET is $^{18}$F-labeled TKTL1. The invention further relates to methods of synthesizing labelled substrates and to compositions comprising such analogues.

In course of the experiments leading to the present invention it was further found that mutations of TKTL1 (e.g. during evolution of mammals, a deletion of an exon encoding 38 amino acids happened in TKTL1) not only result in the lowering of substrate specificity but, in addition, in a lower affinity for thiamine. Thus, a reduced thiamine level leads to an increased failure of some of the TKTL1 proteins resulting in damages being due to decreased TKTL1 activity. These pathological changes can be avoided or at least corrected by activation of this metabolic pathway. Determination of thiamine affinity of TKTL1, or amount of TKTL1 or activity of TKTL1 can be exploited to identify individuals who should be treated with thiamine or thiamine-derivates which a better bioavailability (e.g. benfotiamine).

Such individuals may be, for example diabetes patients having diabetes associated phenomenons like retinopathy, (cardiac autonomic) neuropathy, or damaging of endothelial cells.

In consequence the present invention further relates to a method for controlling the mam-aGF in an mammalian subject (patient) in need of such controlling, wherein the controlling comprises administering of an effective amount of at least one inhibitor or activator of the activity or concentration of the enzyme TKTL1.

With other words: The present invention further relates to the use of an inhibitor or activator of the activity or concentration of the enzyme TKTL1 for manufacturing a pharmaceutical composition for the inhibition or activation of the mam-aGF, i.e. for therapeutic treatment or controlling of diseases associated with an decreased or enhanced mam-aGF.

This technical teaching is based on the scientific finding (in course of the novel and surprising discovery of the mam-aGF), that a further important property of the TKTL1 enzyme is its appropriateness as a target molecule for an inhibitor or activator of the mam-aGF.

The treatment of disorders associated with overexpression of TKTL1 gene may comprise any method suitable for the reduction of the activity of TKTL1 polypeptide in an individual or in cells of an individual. These methods may comprise a reduction of the activity of TKTL1 polypeptide by means of reduction of gene expression or by means of reduction of enzymatic activity. Examples may comprise the administration of antisense constructs, of ribozymes, of enzyme inhibitors, the administration of antagonists of cofactors of TKTL1 polypeptides, such as e.g. antithiamine compounds or the reduced administration of essential cofactors for the enzymatic activity (e.g. thiamine).

A preferred therapy of disorders associated with the overexpression of TKTL1 gene comprises administration of antithiamine compounds or the reduction of thiamine uptake for individuals showing disorders characterized by overexpression of TKTL1 gene.

In consequence the present invention also comprises a pharmaceutical composition comprising an effective amount of an inhibitor or activator of the activity or concentration of the enzyme TKTL1 and a pharmaceutically acceptable carrier.

A preferred embodiment of such a pharmaceutical composition comprises a TKTL1 inhibitor elected from the group consisting of oxythiamine, benfooxytiamine (=oxybenfotiamin), hydroxypyruvate, pyruvate, p-hydroxyphenylpyruvate, pyrithiamin, amprolium, 2-methylthiamin, 2-methoxy-p-benzochinon (2-MBQ) and 2,6-dimethoxy-p-benzochinon (2,6-DMBQ), genistein, and flavonols as e.g. quercetin, catechins, nitrilosides, anthocyanins; or derivatives thereof.

A preferred embodiment of such a pharmaceutical composition with TKTL1 inhibitor effect comprises one or more Amprolium derivatives having the chemical structure (structural formular):

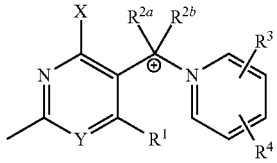

and/or at least one Flavonol having the chemical structure (structural formular):

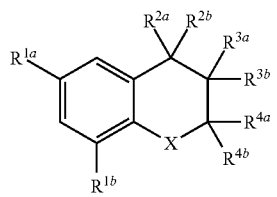

Another preferred embodiment of a pharmaceutical composition with TKTL1 inhibitor effect comprises one or more thiamin and/or benfotiamin derivatives having the chemical structure (structural formular)
(a):

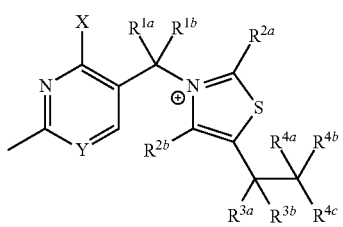

for thiamine derivatives
and (b):

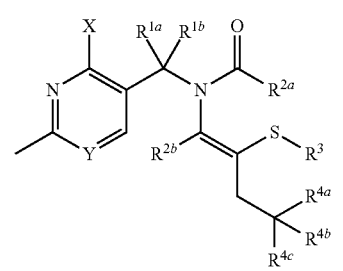

for benfotiamine derivatives.

One preferred inhibitory benfotiamine derivative is oxybenfotiamine (=benfooxytiamin) having the chemical structure (structural formular):

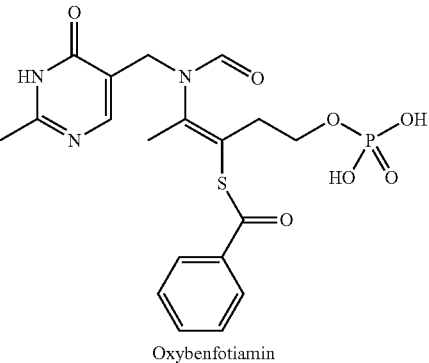 [SMILES: C/C(=C(/CCOP(=O)(O)O)SC(=O)c1ccccc1)N(C=O)Cc1cnc(C)[nH]c1=O]

Oxybenfotiamin

A preferred embodiment of a pharmaceutical composition with TKTL1 activator effect comprises thiamine and/or benfotiamine and/or functionally equivalent, i.e activating, derivates thereof.

The activating thiamine derivatives preferably have the chemical structure (structural formula):

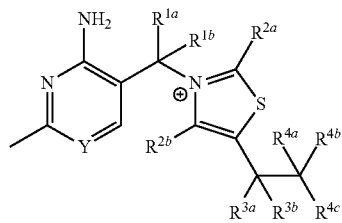

And the activating benfotiamin derivates preferably have the chemical structure (structural formula):

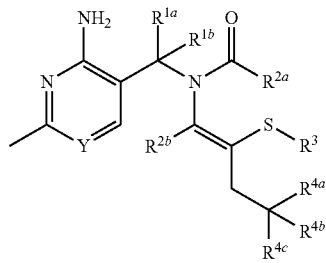

Derivatives of the above listed activators or inhibitors can be generated by substituting or adding one or more of the following groups:

linear and branched ($C_1$-$C_{12}$) aliphatic alkyl groups, substituted with at least one group chosen from OH, $NH_2$, SH, CN, $CF_3$, halogen, $CONHR^5$, $COOR^5$, $OR^5$, $SR^5$, $SiOR^5$, $NHR^5$, aliphatic ($C_3$-$C_6$) rings, and aromatic ($C_3$-$C_6$) rings, wherein $R^5$ is chosen from linear and branched ($C_1$-$C_4$) alkyl groups, aryl groups, natural polymers, synthetic polymers, and copolymers, said polymers and copolymers carrying at least two groups chosen from: hydroxyl, carboxylate, primary amine, secondary amine, tertiary amine, thiol, and aldehyde;

a hydrogen atom, a halogen atom, $CF_3$, OH, $OCF_3$, COOH, $R^7$, $OR_7$, and $OCOR^7$, wherein $R^7$ is chosen from linear and branched ($C_1$-$C_4$) aliphatic alkyl groups;

a monohalogenated and polyhalogenated linear and branched ($C_1$-$C_4$) alkyl groups, and from aryl groups, wherein the aryl groups are optionally substituted with at least one group chosen from OH, $NH_2$, SH, CN, $CF_3$, halogen, COOH, $CONHR^8$, $COOR^8$, $OR^8$, $SR^8$, and $NHR^8$, wherein $R^8$ is chosen from linear and branched ($C_1$-$C_{12}$) alkyl radicals; and from linear and branched ($C_1$-$C_4$) alkyl groups, and a $CF_3$ group.

The TKTL1 inhibitors or activators may also be realized in form of one or more nucleic acid molecules, recombinant vectors, polypeptides, antisense RNA sequence, ribozymes and/or antibodies.

Therefore another pharmaceutical composition of the present invention which is suitable for the prevention or treatment of a disease associated with an abnormal cellular localization of the mutated TKTL1 protein, aggregation status and/or dimerization status (compared to a control contraception) is characterised in that it comprises an effective amount of a nucleic acid molecule, a recombinant vector, a polypeptide, an antisense RNA sequence, a ribozyme or an antibody.

This pharmaceutical composition may for example contain DNA that codes for a functional TKTL1. The DNA may be administered in a way that allows the polypeptides to be generated in situ. Suitable expression systems are known to those skilled in the art. Transgenic mammalian cells may be used for delivery and/or expression of the nucleic acids. The appropriate methods are known to those of skill in the art.

Alternatively, the pharmaceutical compositions may comprise one or more polypeptides. The polypeptides incorporated into pharmaceutical compositions may be the TKTL1 polypeptides in combination with one or more other known polypeptides such as for example enzymes, antibodies, regulatory factors, such as cyclins, cyclin-dependent kinases or CKIs, or toxins.

When blood sugar levels rise, some key kinds of cell—including nerve cells (neurons) and the cells that make up the fine blood cells of the retina of the eye and the filtering units (glomeruli) of the kidney—are also flooded with glucose. The resulting high sugar levels within these cells cause a log jam in the normal cellular metabolism of glucose. This backlog results glucose associated cell damages and in a buildup within the cell of super-reactive glucose-metabolic intermediates known as triosephosphates leading to advanced glycation end products (AGE). And once that happens, the excess glucose and triosephosphates attack the surrounding proteins, lipids, and DNA within the cell.

An enhancement of the mam-aGF by activating the TKTL1 could be a corrective and preventive in that situation. By the mam-aGF pathway glucose is degraded to nontoxic compounds like fatty acids therefore avoiding advanced glycation end product damages.

Therefore, the invention relates to a method for the treatment of glucose and triosephosphate associated cell damages and prevention of AGE-associated cell damages in a patient in need of such treatment comprising administering an effective amount of at least one TKTL1 activator to said patient.

With other words: Therefore the invention also relates to the use of at least one TKTL1 activator for manufacturing a pharmaceutical composition for the treatment and prevention of AGE-associated cell damages in a patient.

A defection/disturbance of the mam-aGF pathway is not generally associated with a serious disease but sometimes merely associate with disturbances of the physical stage which indeed are subjective unpleasant, but do not need a medical treatment. Furthermore the mam-aGF pathway can be controlled not only by activating or inhibiting the TKTL1 enzyme but also by limiting the substrate (glucose) for this metabolic pathway. Therefore the present invention further provides nutrient compositions/dietary supplements containing a low glucose/carbohydrate content, a high oil/fat content and a moderate protein content and further comprising an effective amount of an inhibitor or activator of the activity or concentration of the enzyme TKTL1 and a pharmaceutically acceptable carrier.

A preferred embodiment of such a nutrient composition/dietary supplement comprises a TKTL1 inhibitor elected from the group consisting of oxythiamine, benfooxytiamine, hydroxypyruvate, pyruvate, p-hydroxyphenylpyruvate, pyrithiamin, amprolium, 2-methylthiamin, 2-methoxy-p-benzochinon (2-MBQ) and 2,6-dimethoxy-p-benzochinon (2,6-DMBQ), genistein, and flavonols as e.g. quercetin, catechins, nitrilosides, anthocyanins; or derivatives thereof.

An other preferred embodiment of such a nutrient composition/dietary supplement comprises a TKTL1 activator, especially thiamin or benfotiamine or one or more derivatives thereof. Said derivatives are preferably characterised by the above-mentioned chemical structure (structural formulas).

The present invention also relates to the use of a compound for the treatment of a disease associated with an enhanced or decreased level or activity, an abnormal cellular localization of the TKTL1 protein, aggregation status and/or dimerization status compared to a control, wherein said compound is a compound identified by a method comprising the following steps:

(a) contacting a TKTL1 polypeptide as defined in the preceding claims or a cell expressing said polypeptide in the presence of components capable of providing a detectable signal in response to a biological activity, preferably transketolase activity; and (b) detecting presence or absence of a signal or increase of the signal generated from said biological activity, wherein the absence, decrease or increase of the signal is indicative for a putative drug.

The drug candidate may be a single compound or a plurality of compounds. The term "plurality of compounds" is to be understood as a plurality of substances which may or may not be identical. Said compound or plurality of compounds may be chemically synthesized or microbiologically produced and/or comprised in, for example, samples, e.g., cell extracts from, e.g., plants, animals or microorganisms. Furthermore, said compound(s) may be known in the art but hitherto not known to be capable of suppressing or activating TKTL1 polypeptides. The reaction mixture may be a cell free extract or may comprise a cell or tissue culture. Suitable set ups are known to the person skilled in the art. The plurality of compounds may be, e.g., added to the reaction mixture, culture medium, injected into a cell or otherwise applied to the transgenic animal. The cell or tissue that may be employed in the method of the invention preferably is a host cell, mammalian cell or non-human transgenic animal of the invention described in the embodiments hereinbefore.

If a sample containing a compound or a plurality of compounds is identified in the method of the invention, then it is either possible to isolate the compound from the original sample identified as containing the compound capable of suppressing or activating TKTL1, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the present method only comprises a limited number of or only one substance(s). Preferably said sample comprises substances of similar chemical and/or physical properties, and most preferably said substances are identical.

The compounds which can be tested and identified may be peptides, proteins, nucleic acids, antibodies, small organic compounds, hormones, peptidomimetics, PNAs or the like. These compounds may also serve as lead compounds for the development of analog compounds. The analogs should have a stabilized electronic configuration and molecular conformation that allows key functional groups to be presented to the TKTL1 in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989).

As known up to now the novel discovered mam-aGF is regularly (normally, natively) present in healthy tissues like retina, endothelial cells, nervous tissue and testis.

In the course of the experiments leading to the present invention it became obvious that in several tumor tissues the mam-aGF proceeds with high turn-over. In these tumor cells an overexpressing of the TKTL1 enzyme was detected and likewise large amounts of lactate leading to a matrix degradation. These findings confirm the studies of Warburg, who detected that not only in the absence of oxygen but also in the presence of oxygen tumor tissue degrades glucose to lactate, and that there is a correlation between the degree of aerobic fermentative glucose degradation (aerobic glycolysis), lactate production and malignancy. By transcript and protein based analysis of the three TKT family members it could be demonstrated, that the TKTL1 gene is the transketolase gene/protein which is overexpressed in tumors.

Therefore the present invention also comprises a method for the treatment of cancer associated with an overexpression of TKTL1 enzyme in the tumor cells in a patient in need of such treatment comprising administering an effective amount of at least one TKTL1 inhibitor to said patient.

With other words: Therefore the invention also relates to the use of at least one TKTL1 inhibitor for manufacturing a pharmaceutical composition for the treatment of cancer associated with an overexpression of TKTL1 enzyme in the tumor cells.

Since it is known that large amounts of lactate lead to a matrix degradation and that this facilitates tissue remodeling and wound healing, the data and knowledges obtained in the course of the experiments leading to the present invention result in a further part of the invention, namely in a method for treatment (or influencing the processes) of tissue remodeling, wound healing etc in a patient in need of such treatment comprising administering an effective amount of at least one TKTL1 inhibitor or TKTL1 activator to said patient.

With other words: The invention also relates to the use of at least one TKTL1 inhibitor or TKTL1 activator for manufacturing a pharmaceutical composition for enhancing or reducing the processes of tissue remodeling, wound healing etc.

An embodiment of such pharmaceutical composition comprising at least one TKTL1 inhibitor is intended to be applied in restenosis in heart valves to prevent proliferation of endothelial cells.

Since many years transketolase proteins and transketolase enzyme activities have been related to neurodegenerative diseases like Wernicke-Korsakoff syndrome, Alzheimer disease patients, etc. However, the question, how this relation looks like remains open until completion of the present invention.

In the course of the experiments leading to the present invention it was found, that both, patients with Alzheimer disease and patients with Wernicke-Korsakoff syndrome, have reduced TKTL1 enzyme activities and TKTL1 protein variants with different isoelectric points or smaller size. In patients with Wernicke-Korsakoff syndrome it could be demonstrate that their cells do harbor TKTL1 protein isoforms with a reduced affinity for thiamin. Since glycation (e.g. glucose is covalently bound to the proteins—the chemical reaction is known as Schiff's base reaction) is one of the processes involved in amyloidogenesis and protein plaque generation leading to neurodegenerative diseases (for example: the fibrils present in Alzheimer's disease patients share several properties common to glycated proteins and glycation causes the structural transition from folded, soluble form to beta-fibrils) reduced TKTL1 enzyme activities results in an enhancement of glycation and finally in enhanced amyloidogenesis and protein plaque generation.

Due to these facts the present invention also comprises a method for treatment of neurodegenerative diseases like Wernicke-Korsakoff syndrome, Alzheimer disease etc. by inhibiting glycation via activation of the mam-aGF in a patient in need of such treatment comprising administering an effective amount of at least one activator of TKTL1 enzyme activity to said patient (e.g. thiamin or benfotiamine application in food).

Furthermore, enhancing the TKTL1 activity and thereby the mam-aGF can prevent the development of Alzheimer's disease in individuals with a predisposition due to TKTL1. Thus, the present invention further comprises a method to determine individuals with TKTL1 predisposing variants to identify individuals eligible for a preventive TKTL1 therapy.

In this context it should be mentioned that unwanted apoptosis in cells like neurons can be reduced or blocked by treatment of TKTL1 with activating compounds identified by the methods according to the invention.

For patients with diabetes mellitus it has been shown recently that benfotiamine treatment of such patients effects the blockade of three major pathways of hyperglycemic damage and prevents diabetic retinopathy. Now, in the course of the experiments leading to the present invention the inventors were able to identify the TKTL1 enzyme as the target of that benfotiamin treatment in those tissues (endothelial cells, retina, and nerves) in which patients with diabetes get cell damage due to AGE (advanced glycation end-product) formation or cell death.

AGE is also caused by an excess of glucose and triose-phosphates within cells. An enhancement of the mam-aGF by activating the TKTL1 would result in a degradation of glucose and triosephosphates.

Due to these facts the present invention also comprises a method for the treatment of AGE in patients, especially diabetes patients, in need of such treatment, comprising administering an effective amount of at least one activator of TKTL1 enzyme activity to said patient, preferably benfotiamine.

In the course of the experiments leading to the present invention it was further found that reducing the TKTL1 activity can cause growth retardation and preferential reduction of adipose tissue. By inhibition of TKTL1 in adipose tissue obesity can be treated.

Diseases like systemic lupus erythematosus (SLE), rheumatoid arthritis, multiple sclerosis (MS), fibromyalgia, crohn's disease, irritable bowel syndrome (IBS) have steadily risen for the past 80 years. Targeting TKTL1 lead to a significant decrease in levels of auto-antibodies in patients with autoimmune diseases.

The present invention will be explained by means of the following examples and figure.

(B) Expression of TKTL1 protein isoforms in five tumor cell lines derived from four different tumor entities.

(C) TKTL1 full length protein expressed in *E. coli*.

Figure 3:
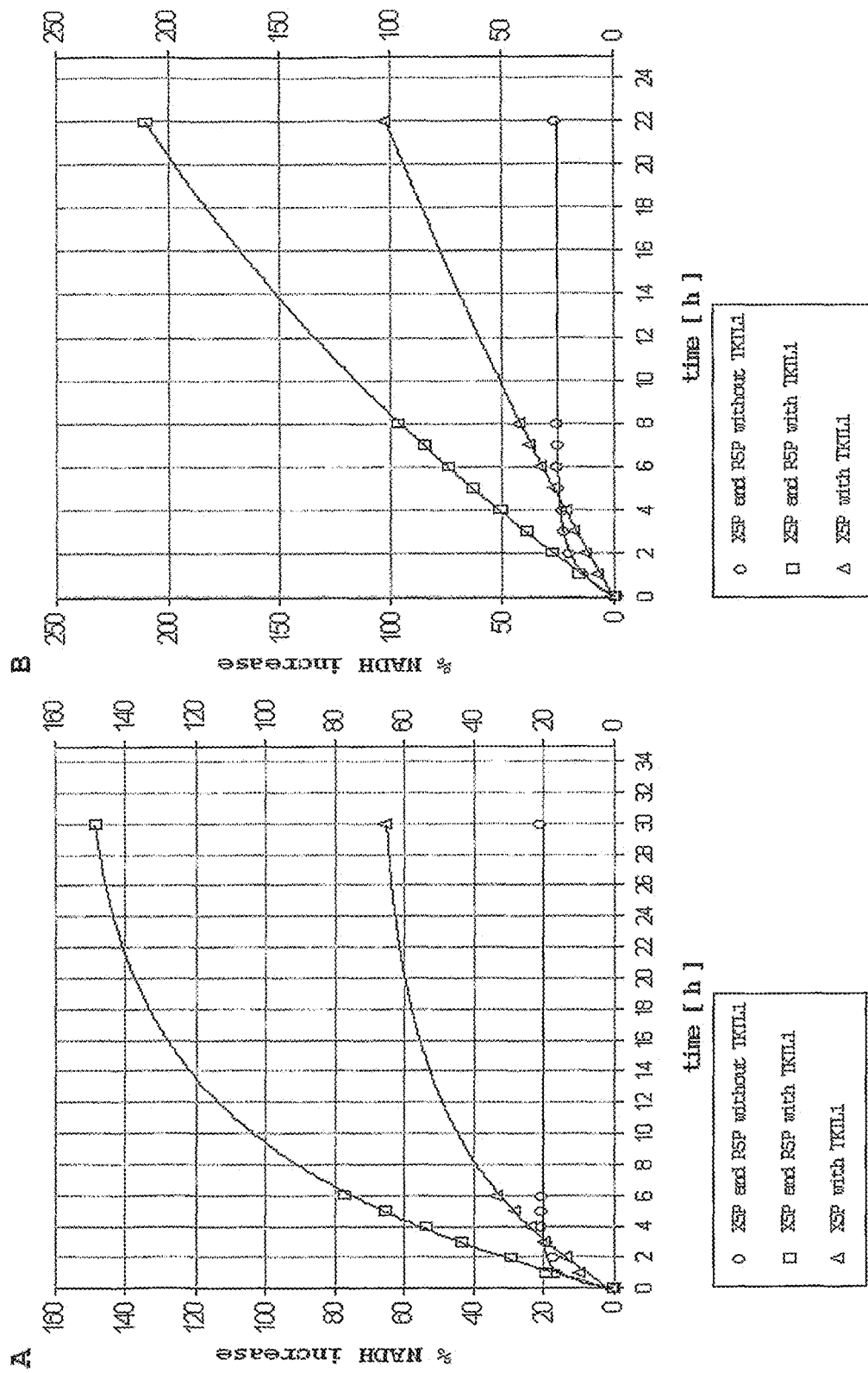

FIG. 3: Determination of transketolase activity of native (A) and recombinant (B) TKTL1 protein.

Figure 4:
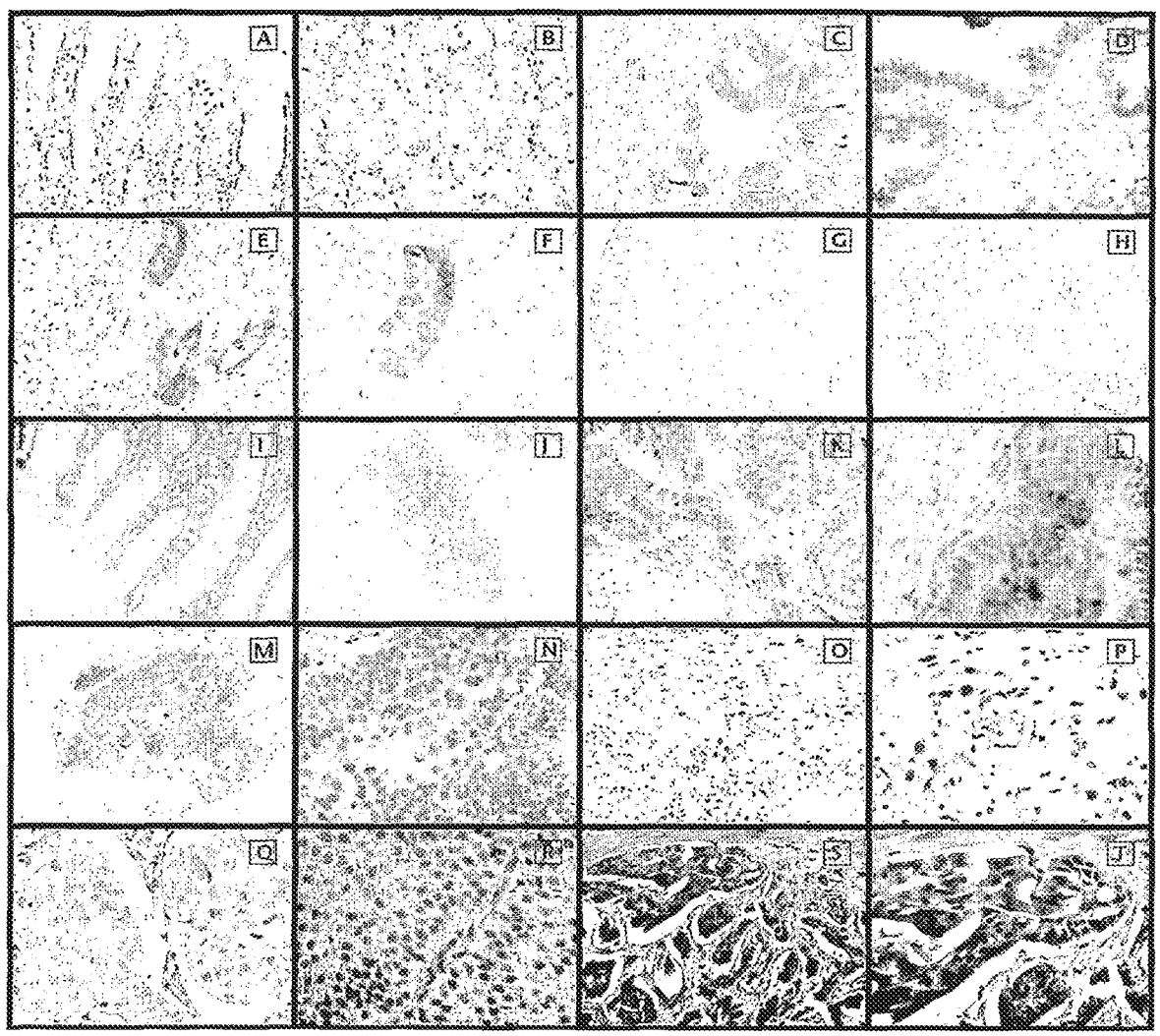

FIG. 4: TKTL1 protein expression in
A-B: normal corpus tissue of gastric carcinoma patient 1;
C-F: tumor tissue of gastric carcinoma patient 1;
G-I: normal antrum tissue of gastric carcinoma patient 2,
J-N: gastric carcinoma cells of patient 2,
O, P: poorly differentiated gastric carcinoma;
Q: colon carcinoma;
R: superficial bladder carcinoma;
S, T: invasive poorly differentiated bladder carcinoma.
Magnification: G×50; C, H, and J×100; A, B, D, E, I, K, M, O, and S×200; F, L, N, P, Q, R and T×400.

Figure 5:
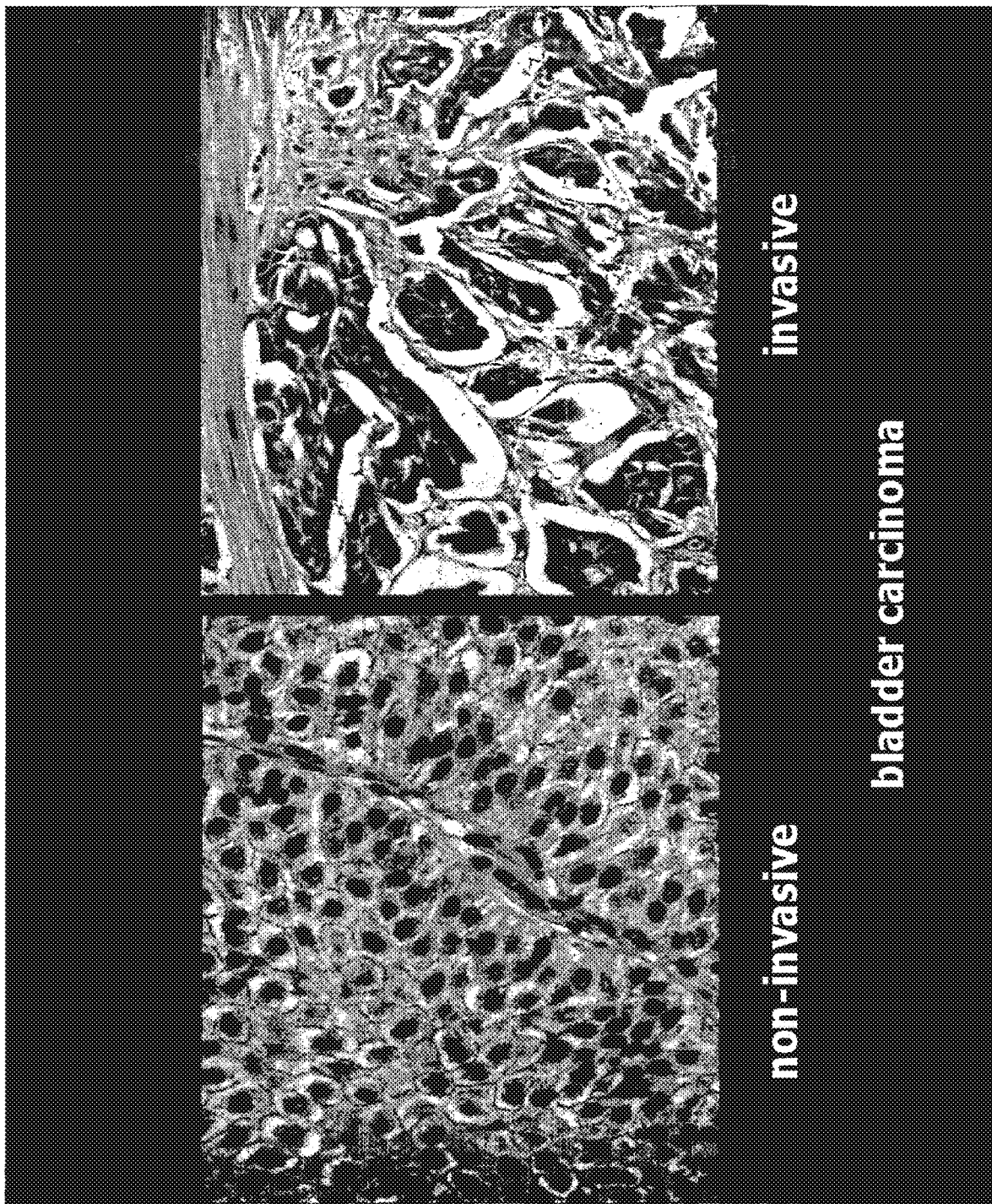

FIG. 5: TKTL1 staining of noninvasive and invasive bladder carcinoma.

Figure 6:
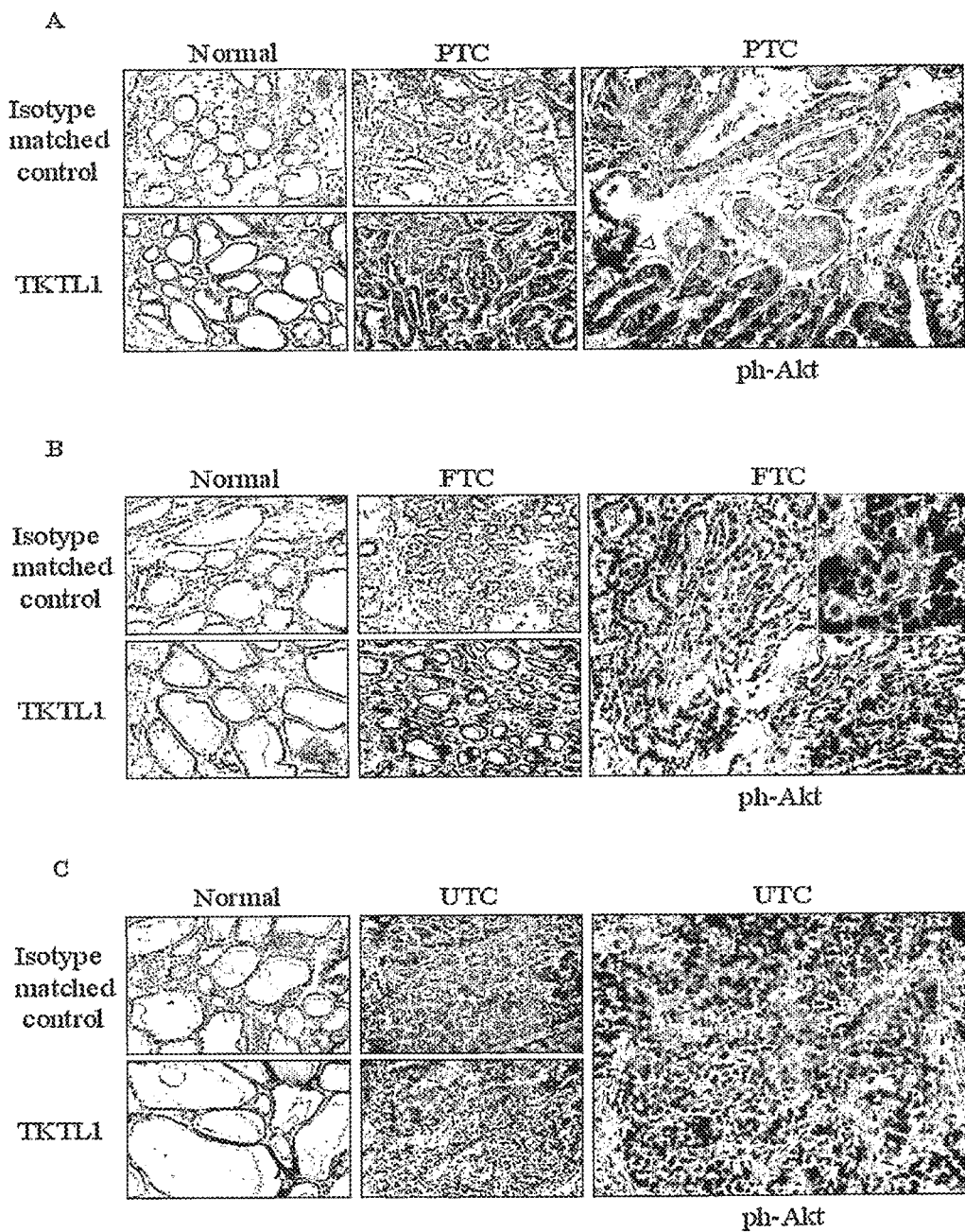

FIG. 6-8: Expression of TKTL1 and phosphorylated Akt (ph-Akt) in paraffin embedded sections of
A-C: normal, papillary (PTC), follicular (FTC), and undifferentiated (UTC) thyroid cancer; D: normal and NSLC tissues, E: colon cancer; F: normal bladder; G: prostate carcinomas.

Figure 10:
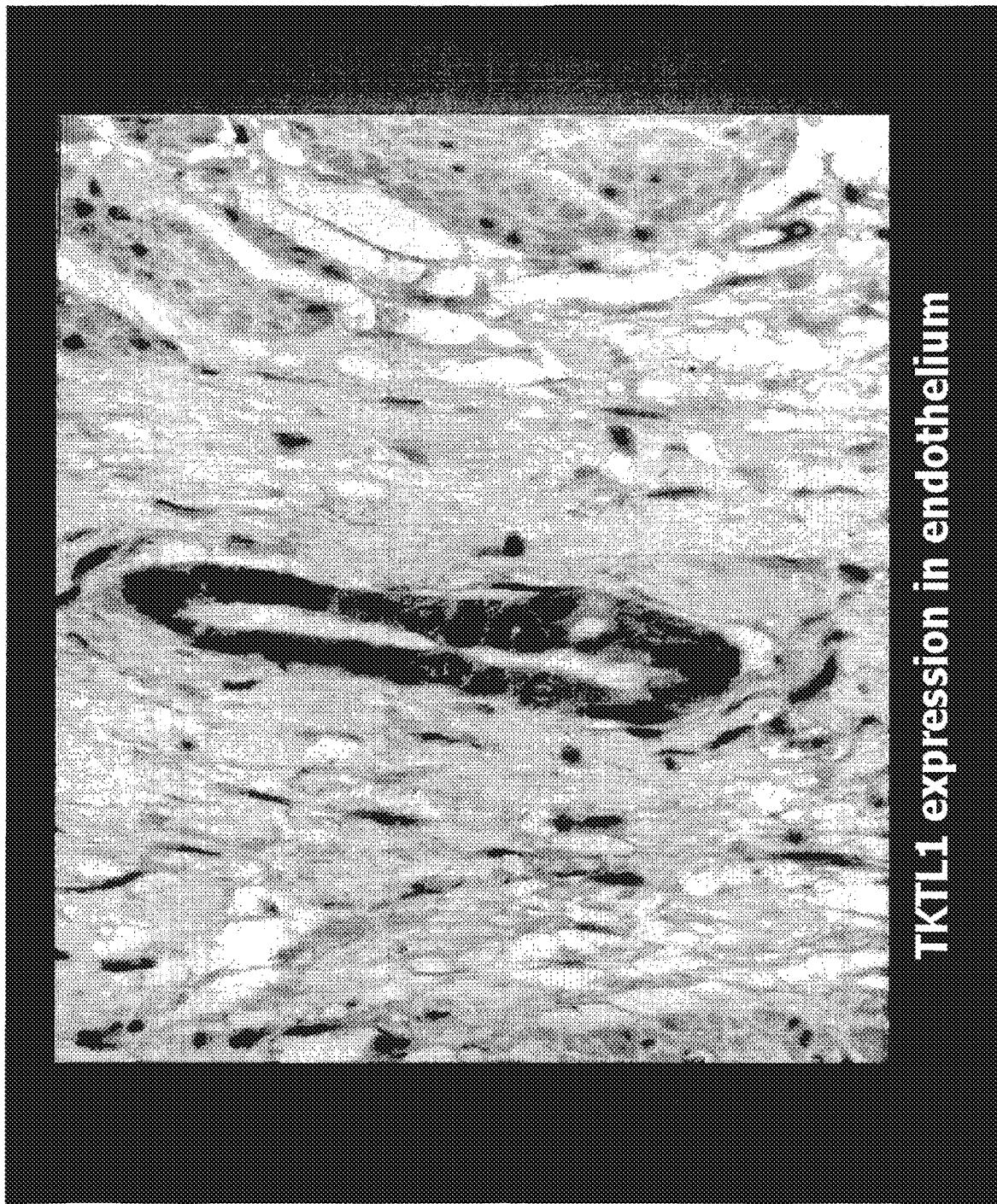
Figure 11:
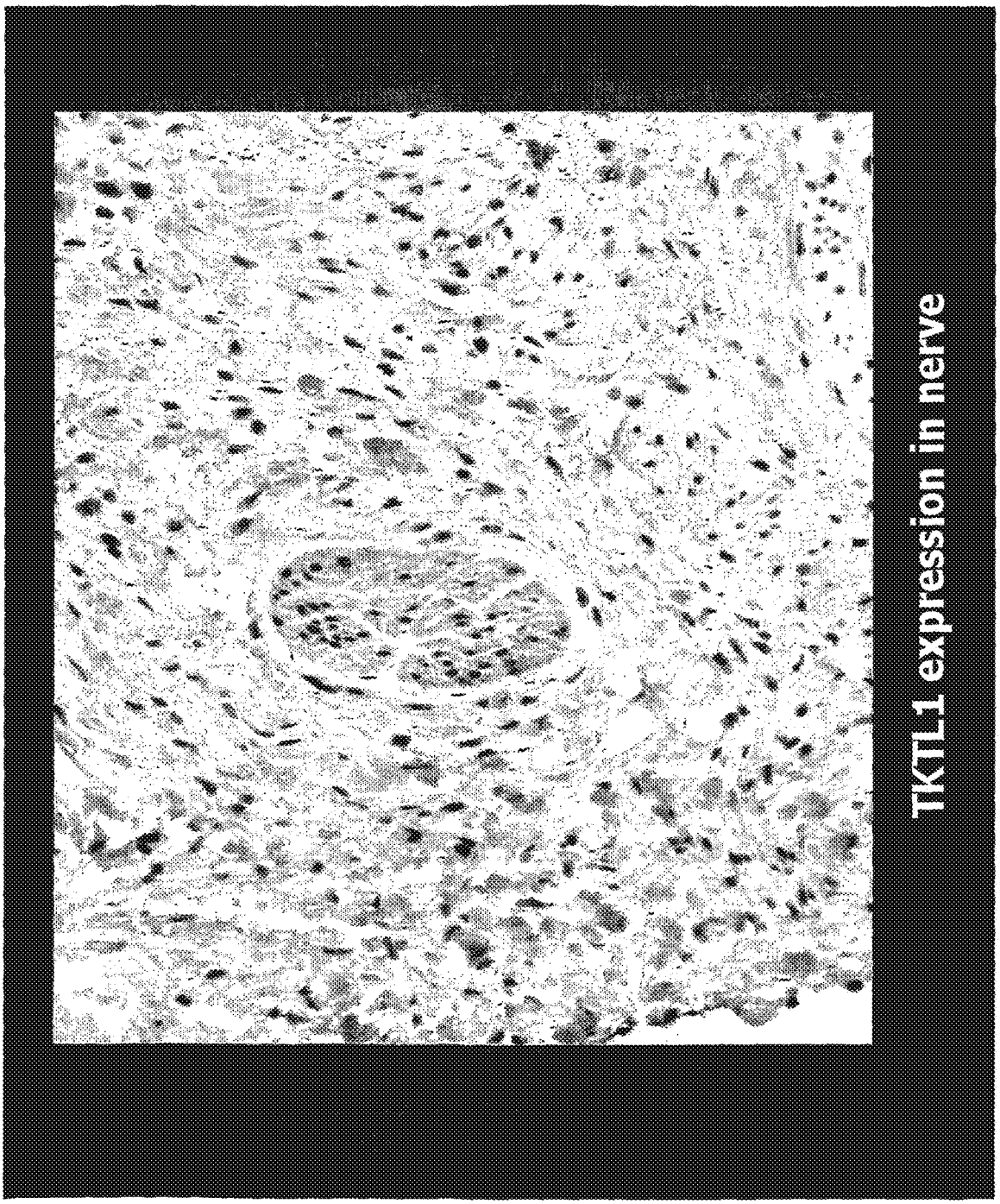
Figure 12:
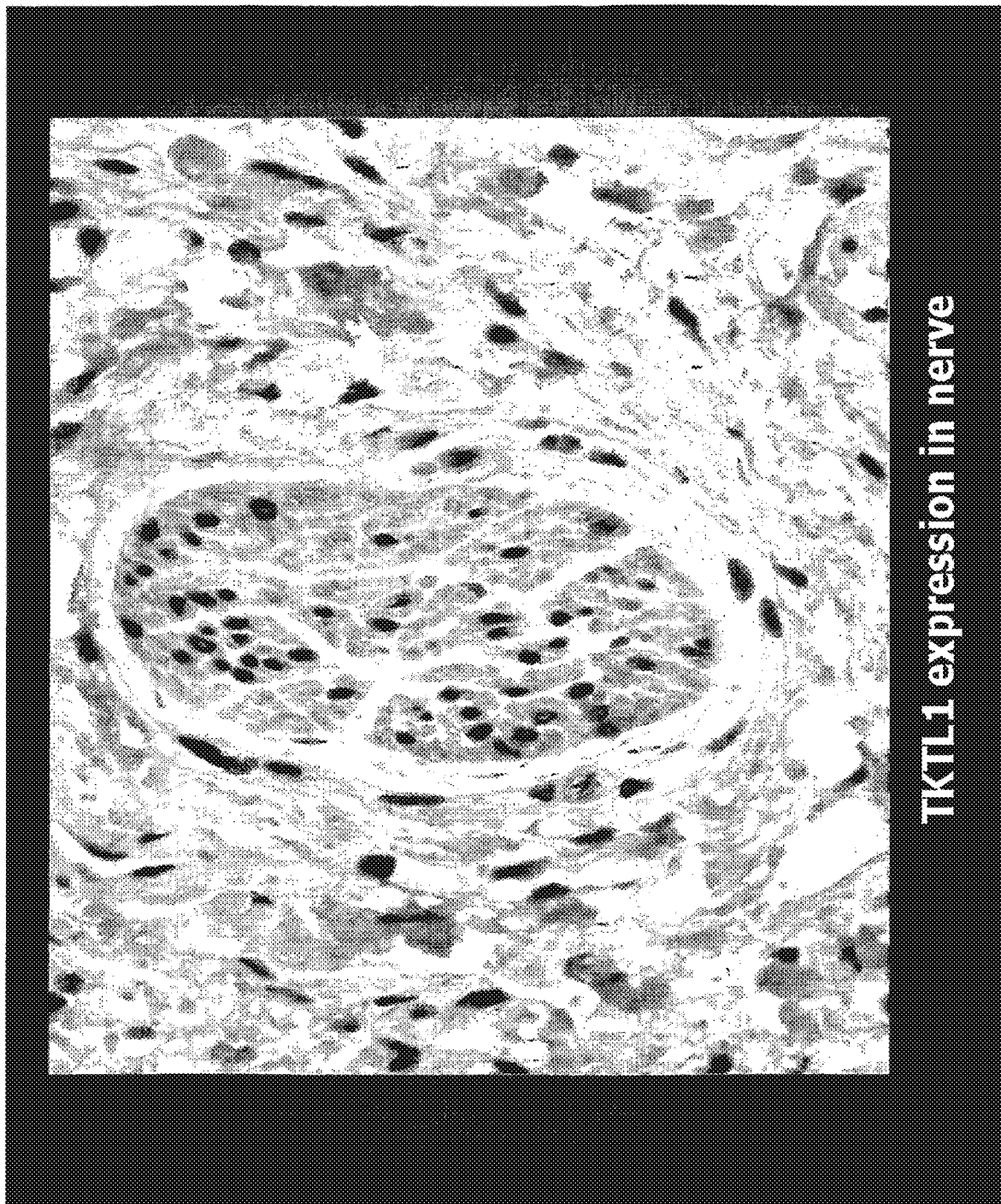
Figure 13:
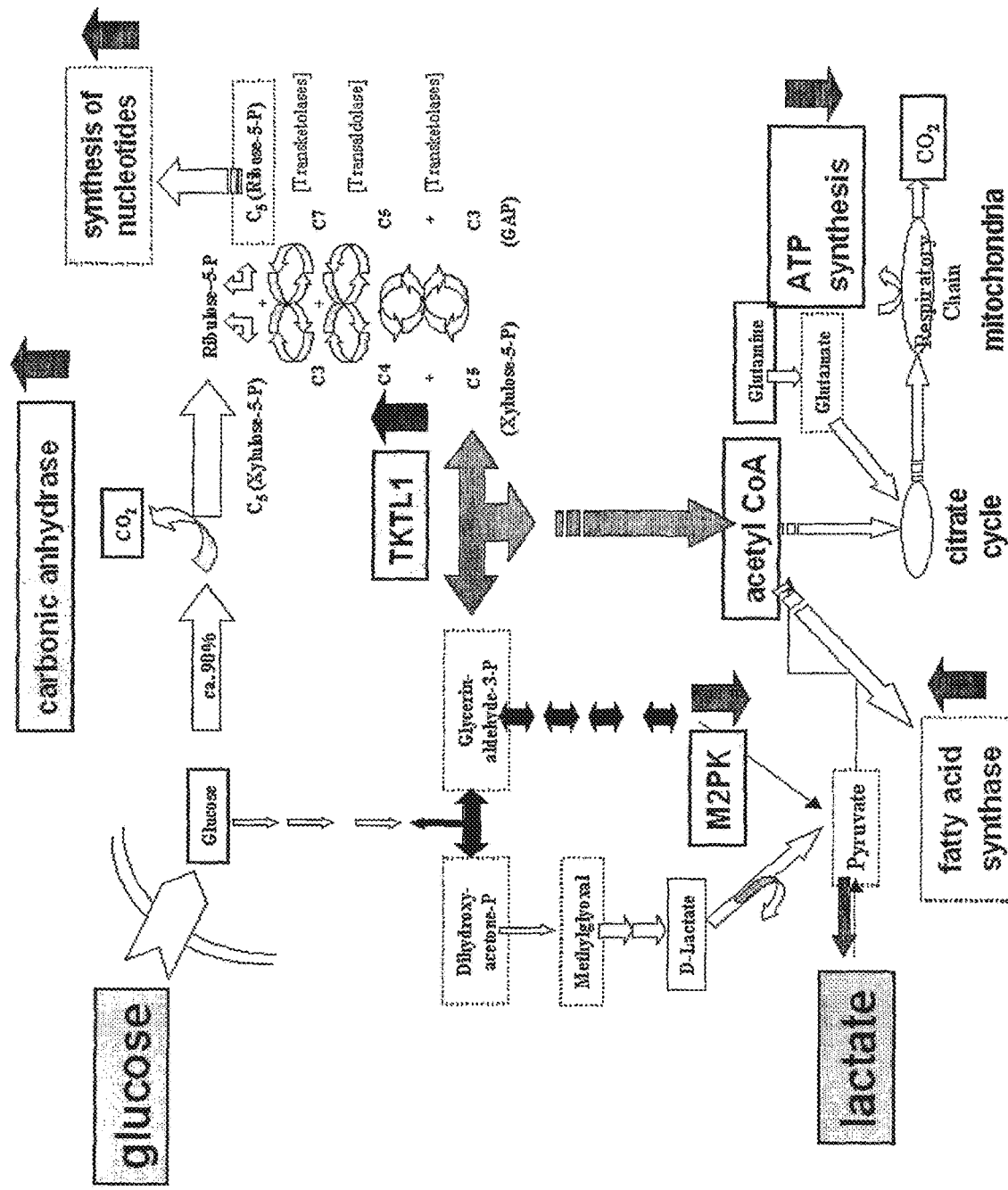
Figure 14:
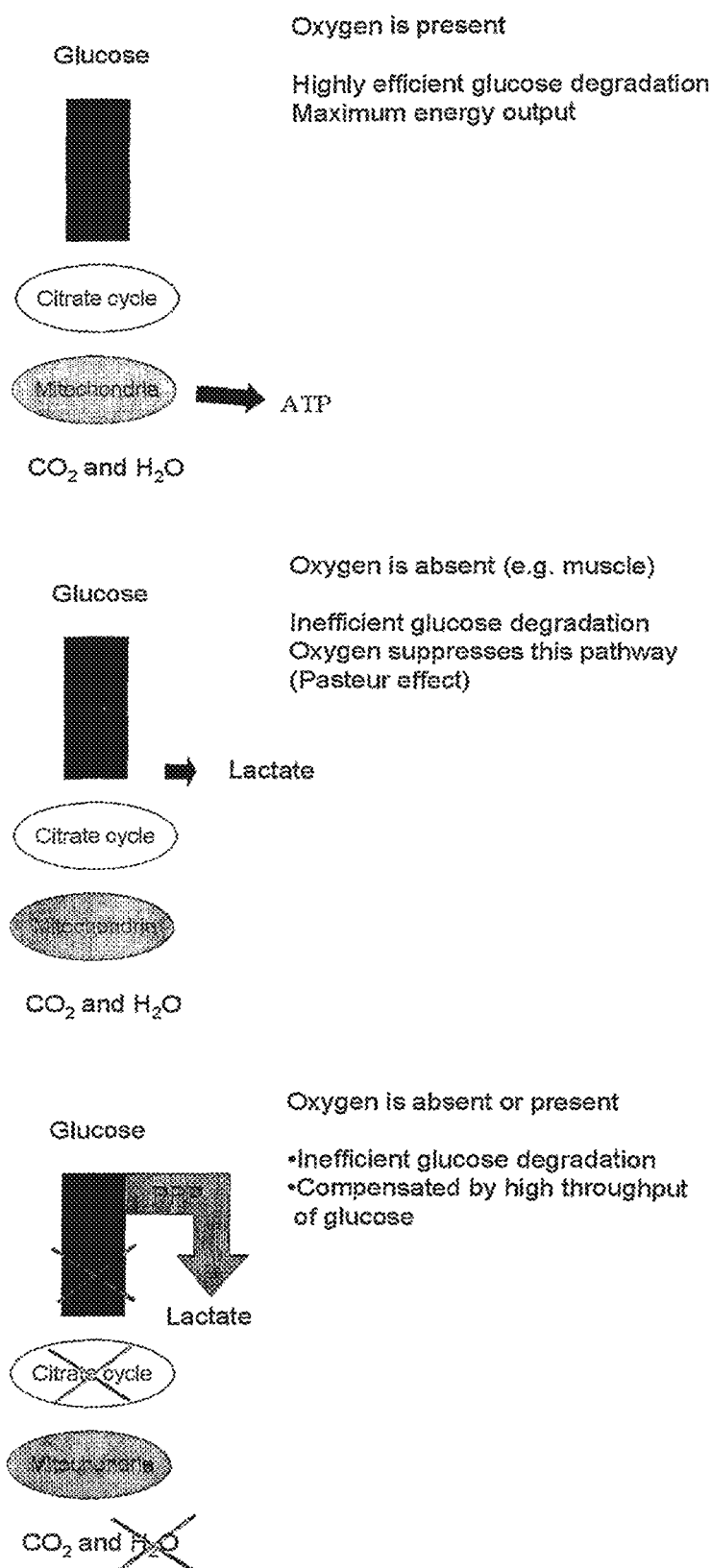
Figure 15:
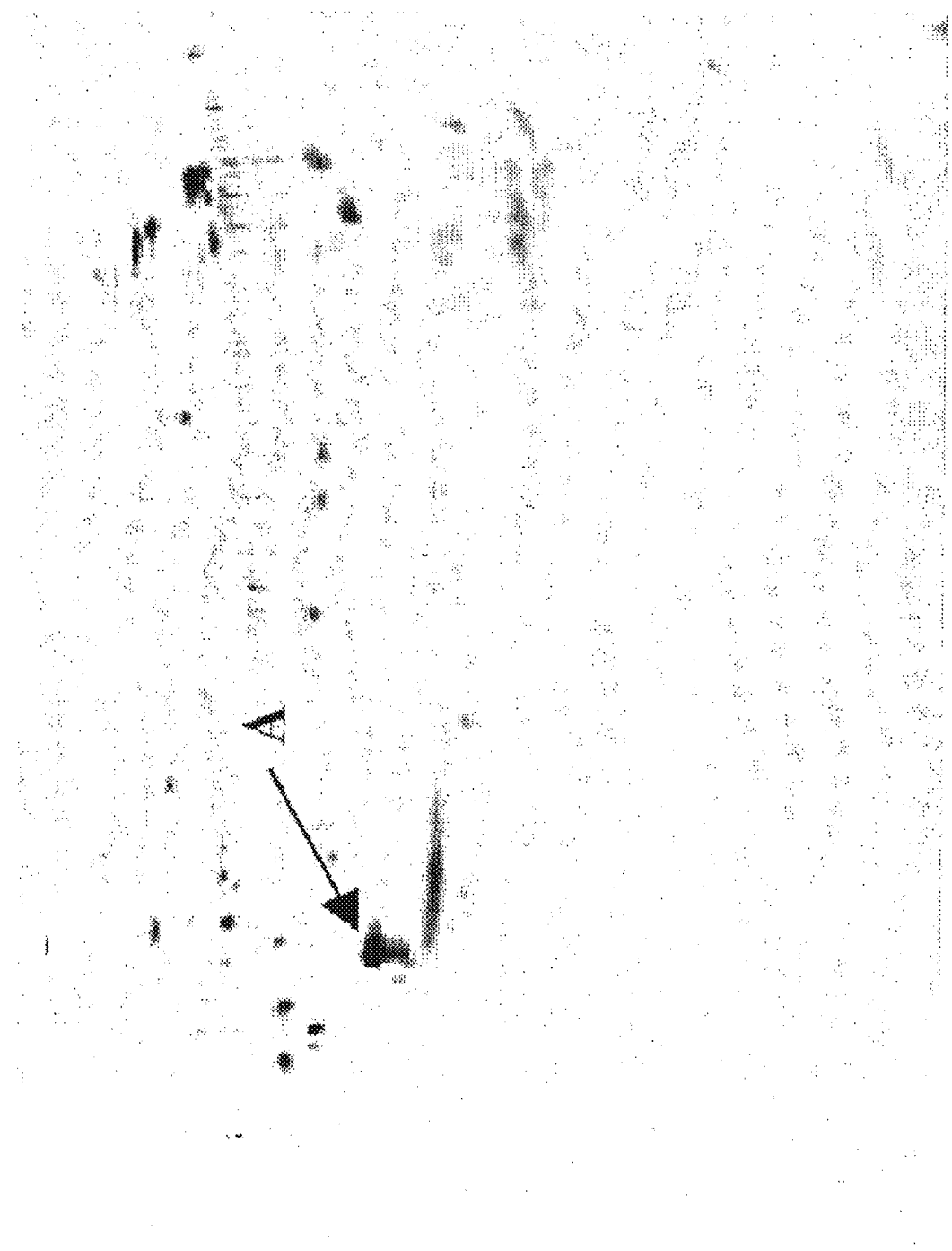

AEC=red staining; Counterstaining with haematoxylin=blue staining, Yellow arrowheads indicate nuclear ph-AKT staining FIG. 9-10: Expression of TKTL1 in endothelial cells.
FIG. 11-12: Expression of TKTL1 in neuronal cells.
FIG. 13-14: schematic drawing of the mam-aGF pathway.
FIG. 15: 2-dimensional (2D)-gel electrophoresis of a multi-protein complex harboring TKTL1 protein isoforms (arrow A), DNaseX, and GAPDH.

Figure 16:
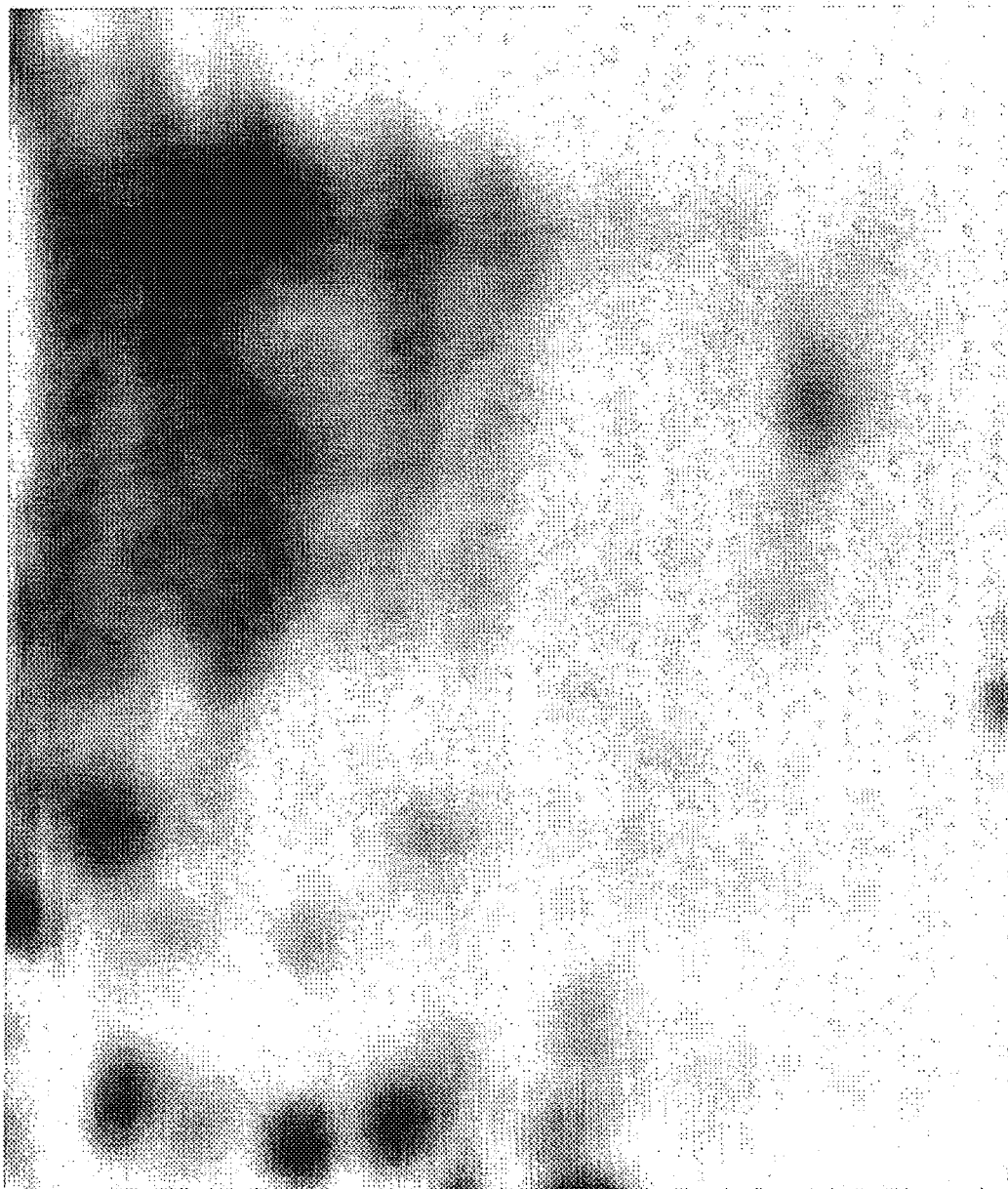

FIG. 16: 2D-gel electrophoresis of high molecular weight TKTL1 protein isoforms (arrow) identified by immunostaining.

FIG. 17: ELISA determination (A) of TKTL1 protein isoforms and (B) of transketolase activity of isolated TKTL1 protein. Values obtained
(A)A1-A5: from leukocytes from healthy persons,
(A)A6-A10: from fibroblasts from healthy persons,
(A)B1-B5: from serum from healthy persons,
(A)B6-B10: from brain cells from healthy persons,
(A)A11-A12: without probe material (background level),
(A)B11-B12: without probe material (background level),
(A)C1-C3: from leukocytes from AD patients,
(A)C4-C6: from fibroblast from AD patients,
(A)C7-C9: from serum from AD patients,
(A)C10-C12: from brain cells from AD patients.
(A)D1-D3: from leukocytes from Morbus Parkinson patients,
(A)D4-D6: from fibroblast from Morbus Parkinson patients,
(A)D7-D9: from serum from Morbus Parkinson patients,
(A)D10-D12: from brain cells from Morbus Parkinson patients,
(A)E1-E3: from leukocytes from Huntington disease patients.
(A)E4-E6: from fibroblast from Huntington disease patients.
(A)E7-E9: from serum from Huntington disease patients,
(A)E10-E12: from brain cells from Huntington disease patients,
(A)F1-F3: from leukocytes from SLE patients,
(A)F4-F6: from fibroblast from SLE patients.
(A)F7-F9: from serum from SLE patients.
(A)F10-F12: from kidney cells from SLE disease patients,
(A)G1-G3: from leukocytes from Morbus Parkinson patients.
(A)G4-G6: from fibroblast from Morbus Parkinson patients.
(A)G7-G9: from serum from Morbus Parkinson patients,
(A)G10-G12: from kidney cells from Morbus Parkinson disease patients,
(A)H1-H3: from leukocytes from diabetes type II Morbus Parkinson patients,
(A)H4-H6: from fibroblast from diabetes type II patients,
(A)H7-H9: from serum from diabetes type II patients,
(A)H10-H12: from kidney cells from diabetes type II disease patients,
(B)A1-A5: from leukocytes from healthy persons,
(B)A6-A10: from fibroblasts from healthy persons,
(B)B1-B5: from serum from healthy persons,
(B)B6-B10: from brain cells from healthy persons,
(B)A11-A12: without probe material (background level),
(B)B11-B12: without probe material (background level),
(B)C1-C3: from healthy persons,
(B)C4-C6: from neuronal cells from healthy persons,
(B)C7-C9: from kidney cells from healthy persons,
(B)C10-C12: from colon cells from healthy persons,
(B)D1-D3: from (B)leukocytes from AD patients,
(B)D4-D6: from fibroblast from AD patients,
(B)D7-D9: from serum from AD patients,
(B)D10-D12: from brain cells from AD patients,
(B)E1-E3: from leukocytes from Morbus Parkinson patients,
(B)E4-E6: from fibroblast from Morbus Parkinson patients,
(B)E7-E9: from serum from Morbus Parkinson patients,
(B)E10-E12: from brain cells from Morbus Parkinson patients,
(B)F1-F3: from leukocytes from SLE patients,
(B)F4-F6: from fibroblast from SLE patients, (B)F7-F9: from serum from SLE patients,
(B)F10-F12: from kidney cells from SLE disease patients,
(B)G4-G6: from fibroblast from multiple sclerosis patients,
(B)G7-G9: from serum from multiple sclerosis patients,
(B)G10-G12: from kidney cells from multiple sclerosis patients,
(B)H1-H3: from leukocytes from diabetes type II patients,
(B)H4-H6: from fibroblast from diabetes type II patients,
(B)H7-H9: from serum from diabetes type II patients,
(B)H10-H12: from kidney cells from diabetes type II disease patients.

GENERAL INFORMATION CONCERNING THE EXAMPLES

Origin and Cultivation of Cells

The lung carcinoma cell line A549, the breast carcinoma cell line MCF7, the liver carcinoma cell line HepG2, and the colon carcinoma cell lines HCT116 and HT29 were obtained from ATCC. Cells were grown in RPMI 1640 or DMEM supplemented with 10% FCS, penicillin and streptomycin (Invitrogen) at 37° C. with 5% $CO_2$.

Northern Blot Analysis

A DNA probe from the 3' untranslated region (residue 1627 to 2368) of the TKTL1 transcript (acc. no. X91817) was labelled with [[alpha]-$^{32}$P]dATP and [[alpha]-$^{32}$P]dCTP (3000 Ci/mmol) in a random primed reaction (Feinberg and Vogelstein, 1983). Hybridization was carried out in 0.5 M sodium phosphate, 7% SDS, 0.2% bovine serum albumin, 0.2% PEG 6000, 0.05% polyvinylpyrrolidone 360000, 0.05% Ficoll 70000 and 0.5% dextran sulphate at 65° C. overnight. Non-specifically bound probe was removed by washing at 65° C. in 40 mM sodium phosphate, pH 7.2, 1% SDS for 60 min. Filters were exposed to X-ray film (Kodak) for 1-5 days. A multiple human adult tissue poly(A)$^+$RNA northern blot was purchased from BD Biosciences Clontech.

Western Blot Analysis

For Western blot analysis, cells were lysed in lysis buffer (50 mM Tris-HCl pH 7.5, 150 mM sodium chloride, 1% NP40, 0.5% sodium deoxycholate, 0.1% SDS, 0.02% sodium azide, 1 mM phenylmethylsulfonyl fluoride). Aliquots of 50 µg of soluble protein was loaded into each well, electrophoresed on 12.5% SDS-polyacrylamide gels, and transferred to polyvinylidene difluoride membranes (Millipore). For detection of TKTL1-proteins the HRP-coupled JFC12T10 MAb was used in a final concentration of 1 µg/ml. The MAb was visualized with an ECL Western blot detection system (Amersham Pharmacia Biotech).

Enzyme-Linked Immunosorbent Assay (ELISA)

TKTL1 protein affinity-purified from cell lines was determined using common standard ELISA techniques. Three different affinity-purified mouse IgG monoclonal anti-TKTL1 antibodies (5 µg/ml) were used for coating of ELISA plates. Horseradish peroxidase conjugated anti-TKTL1 antibody JFC12T10 was used at 5 µg/ml as the secondary reagent. Bound proteins in the multi-protein complex were affinity-purified from cell lines using antibodies directed TKTL1, DNaseX, ph-Akt, GAPDH. Binding to certain proteins was assessed by ELISA technique, using e.g. the combination of TKTL1 and GAPDH antibodies; and the combination of TKTL1 and DNaseX antibodies; and the combination of ph-Akt and DNaseX antibodies.

2D-Analysis of Multi-Protein Complexes

The samples were analysed by high resolution 2D gel electrophoresis (8×7 cm). 2.5 µg of protein was applied to two 2D gels for each sample and 2D gel was stained by silver and the proteins of the second one were transferred to PVDF membranes by semidry electroblotting for immunostaining.

Example 1

Figure 1:
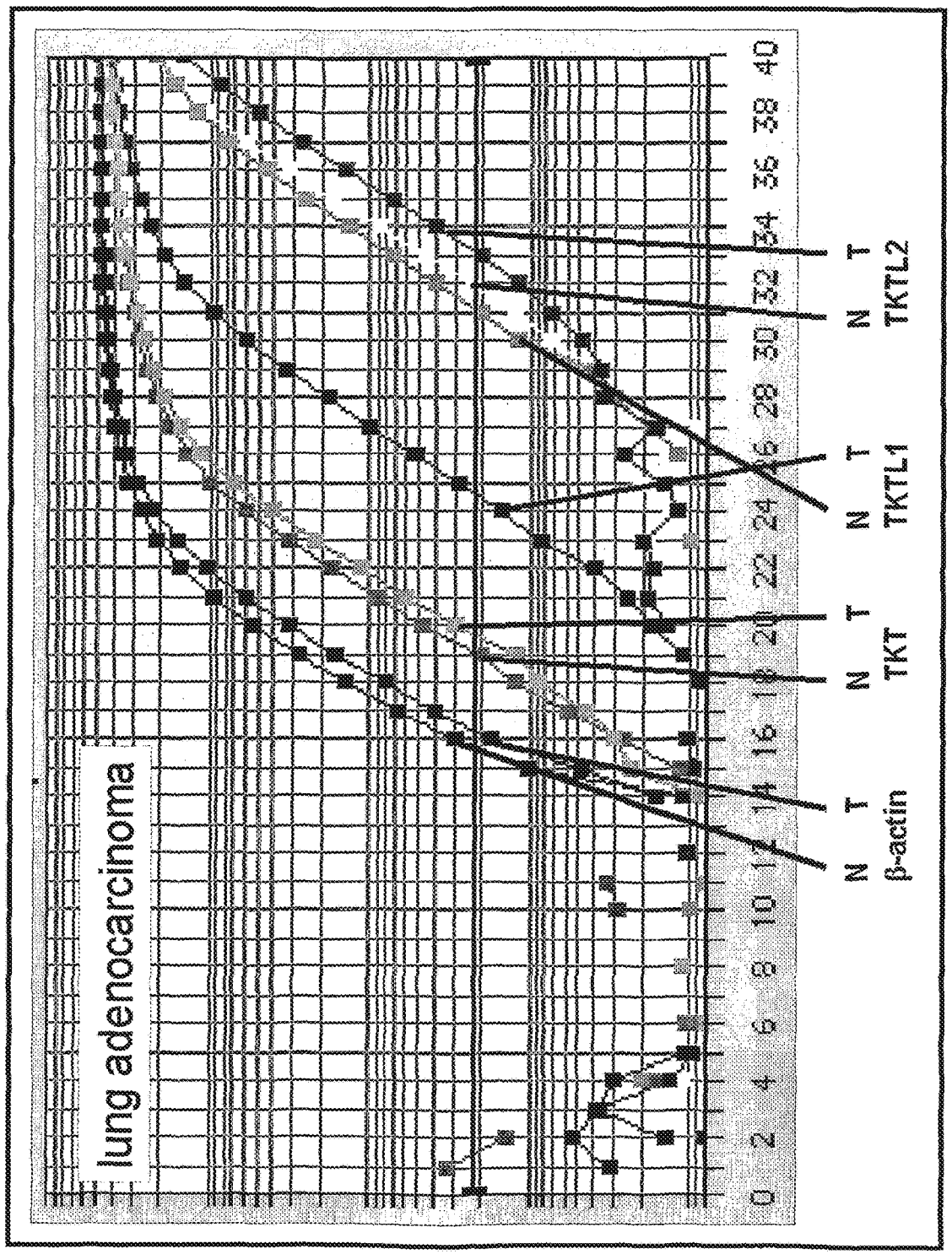
FIG. 1: Quantification of TKTL1 transcripts in gastric and lung adenocarcinoma samples and their corresponding normal tissues. N—normal sample; T—tumor sample; M—marker, 100 by and 200 by fragments are shown.
Figure 2:
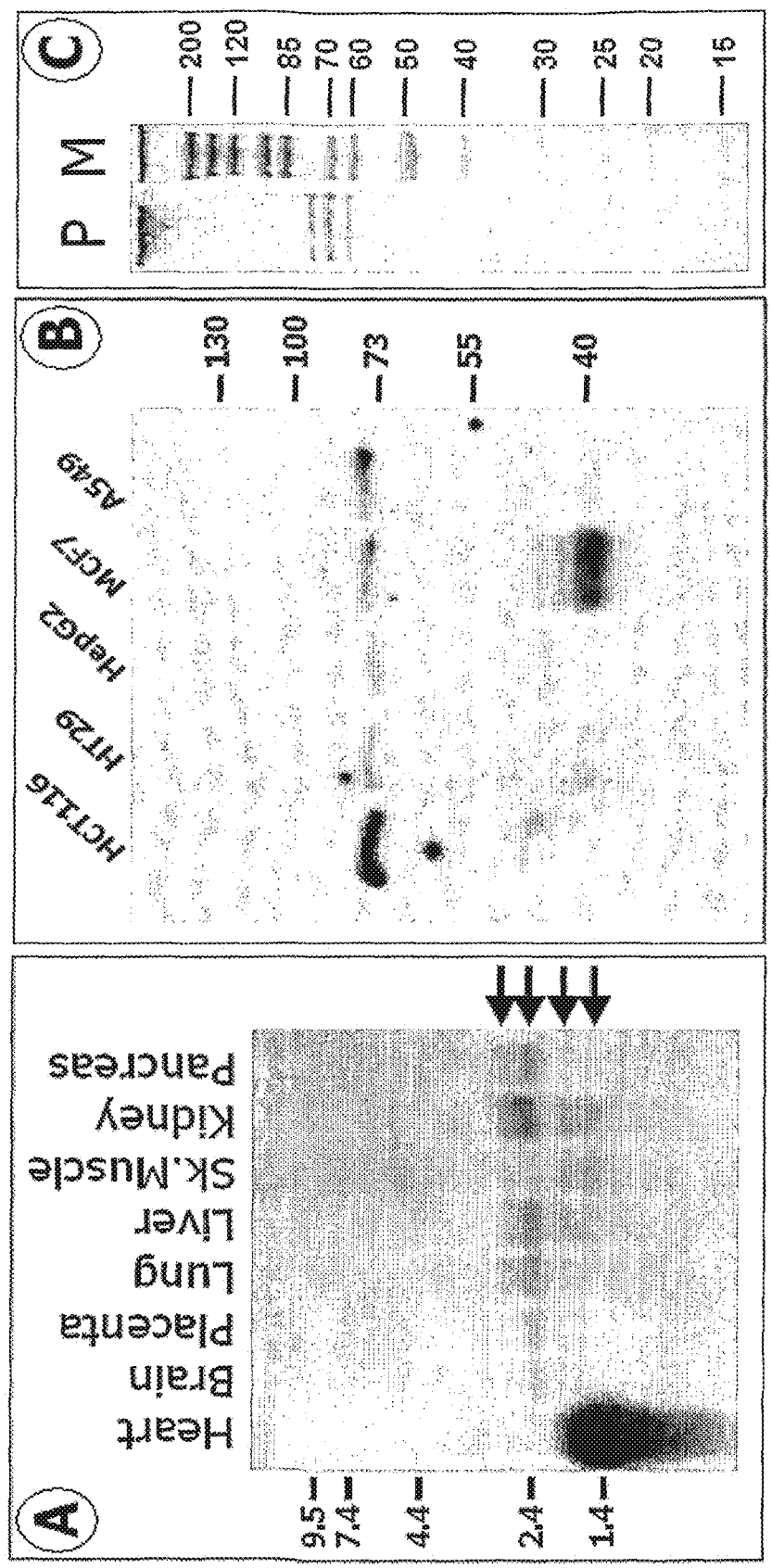
FIG. 2: (A) Expression pattern of the human TKTL1 gene on northern blots of poly(A)⁺mRNA from different human adult tissues analysed with a TKTL1 cDNA probe.

Expression Pattern of the Human TKTL1 Gene on Northern Blots of poly(A)$^+$mRNA from Different Human Adult Tissues Analysed with a TKTL1 cDNA Probe Expression pattern of the human TKTL1 gene was analysed with a TKTL1 cDNA probe on Northern blots of poly(A)$^+$mRNA from different human adult tissues. The results are shown in FIG. 2 (A). Four transcripts of 1.4, 1.9, 2.5, and 2.7 kb are detectable. Whereas the main transcript in most tissues is 2.5 kb in size, in heart the small transcript of 1.4 is abundant and the 2.5 and 2.7 kb transcripts are missing. Transcript sizes are indicated in kb.

Example 2

Isolation and Purification of the TKTL1 Full Length Protein

The TKTL1 full length protein was expressed in E. coli and was isolated by affinity purification through the N-terminal His-tag. One µg of affinity purified TKTL1 protein was loaded onto a 4-20%-gradient SDS gel and stained with Coomassie. Proteins different in size were detected. The largest protein (66 kDa) represents the N-terminal His-tagged full length TKTL1 protein, whereas smaller TKTL1 proteins are likely due to C-terminal proteolytic cleavage already present prior to isolation procedure. Note that the migration of the recombinant 66 kDa His-tagged TKTL1-full length protein indicates a size of 75 kDa. Sizes of the protein marker are indicated in kDa.

Example 3

Determining the Level of TKTL1 Gene Expression in Tissues by Measuring the TKTL1 mRNA Levels Dissections of biopsies can be semi-quantitatively analysed for the mRNA level of TKTL1 gene in an in-situ staining reaction. The staining reaction is performed as follows: The tissue dissections are incubated in ascending ethanol concentrations up to 100% ethanol. After evaporation of the alcohol the dissections are boiled in 10 mM citrate buffer (pH 6.0) for pre-treatment of the tissue. The hybridization mixture is prepared by mixing 50 µl of ready to use hybridization buffer (DAKO A/S, Glostrup, Danmark) with about 5-10 pmol of the probes. The probes are fluorescein-labelled oligonucleotides of the following sequence: TCTCATCACAAGCAGCACAGGAC

Example 4

Determination of Transketolase Activity of Native (A) and Recombinant (B) TKTL1 Protein The two-substrate and one-substrate reaction of native (A) and recombinant (B) TKTL1 protein was determined by the production of NADH as measured by gain in absorbance at 340 nm. Xylulose-5-phosphate (X5P) and ribose-5-phosphate (R5P) were used to determine the two-substrate reaction, whereas X5P alone was used for the one-substrate reaction. In FIG. 3 one representative of three independent enzymatic assays leading to similar results is shown.

Example 5

Determination of TKTL1 Isoforms by ELISA

The combination of TKTL1 antibody JFC6T8 and JFC5T3 determines a TKTL1 protein isoform specifically present in patients with neurodegenerative diseases. The antibodies JFC6T8 and JFC5T3 were coupled to an ELISA plate, and incubated with samples from healthy persons and patients. After removing unspecific bound material, enzymatic activity was determined as described above. High enzymatic activities were obtained in samples of healthy persons. The individual results are listed in FIG. 17 (A)

Example 6

Identification of High Molecular Weight TKTL1 Protein Isoforms by 2D-Gel Electrophoresis High molecular weight TKTL1 protein isoforms from a patient with a neurodegenerative disease (AD) were isolated analyzed by 2D-gel electrophoresis and identified by immunostaining. The results are shown in FIG. 16.

Example 7

Multi-Protein Complex Harboring TKTL1, DNaseX, and GAPDH

The multi-protein complex harboring TKTL1, DNaseX, and GAPDH was affinity-purified from human chronic myelogenous leukemia K562 cells using TKTL1 antibody JFC12T10 coupled to carbo-link. A 2-dimensional (2D)-gel electrophoresis of that multi-protein complex was carried out. TKTL1 protein isoforms (arrow A) and other proteins present in the complex were identified by immunostaining and sequence determination. The results are shown in FIG. 15.

Example 8

Transketolase Activity of TKTL1 Isolated from Healthy and Patient Derived Specimens, Determined with ELISA TKTL1 antibody JFC3T9 was coupled to an ELISA plate, and incubated with samples from healthy persons and patients. After removing unspecific bound material, enzymatic activity was determined as described above. High enzymatic activities were obtained in samples of healthy persons. The individual results are listed in FIG. 17 (B).

Example 9

Assays for Detection of Compounds for Enhancing or Reducing the TKTL1 Enzyme Activity Since the TKTL1 protein isoforms represent moonlighting proteins, different assays for identifying active small compounds have to be applied. Assays for detection of compounds for enhancing or reducing the TKTL1 enzyme activity can be performed by the recombinant protein isoforms or by native protein isoforms isolated from human cells.

(A) Providing Recombinant TKTL1 Protein Isoforms

This can be realized by expression of recombinant TKTL1 protein isoforms in *E. coli*. The TKTL1 open reading frame (MADAE . . . CMLLN) of cDNA sequence (acc. no. BC025382) was cloned into the pDEST17 vector (Invitrogen). Bacterial expression was performed in the *E. coli* strain BL21-AI (Invitrogen), and expression was induced with 0.2% arabinose at 21° C. for 4 h. Crude cell lysate was prepared in lysis buffer (20 mM Tris[pH7.5], 5 mM imidazole, 5 mM beta-mercaptoethanol, 500 mM NaCl, and 1% Triton X-100) by freezing (dry ice, 10 min) and thawing (37° C., 5 min) 3 times. Soluble protein fractions were obtained by centrifugation of the cell lysate at 12.000×g for 30 min at 4° C. His$_6$-TKTL1 protein was purified with Ni-NTA resins (Qiagen) according to the manufacturer's instructions with elution buffer containing 200 mM imidazole. Imidazole and salt were subsequently removed by dialysis against 0.1 M Tris (pH 7.5). The purified enzyme was stored at −20° C. in 40% glycerol and 0.1% dithiothreitol (DTT).

(B) Providing Native Protein Isoforms Isolated from Human Cells

Native TKTL1 proteins and protein complexes harboring TKTL1, both harvested from human cell lines, must be purified, for example via affinity-purification. This can be realized as following:

10 mg of MAb JFC12T10 was coupled to 2 ml carbo-link according to the manufacturer's instructions (carbo-link; Pierce). Cells were grown in serum free media (ISF-1, In Vivo BioTech Services GmbH). After centrifugation, the pellet of 2.2×10$^9$ cells was resolved in 50 ml PBS containing protease inhibitors cocktail (Roche). A cell lysis was performed using a french press, followed by a centrifugation at 50.000×g. The supernatant was filtered (0.2 μm) and binding of supernatant to affinity material was performed over night at 4° C. (batch modus). After transfer to a column, a wash procedure was performed with 150 mM PBS buffer pH 7.4. For elution of column attached proteins 100 mM Glycin-HCl pH 2.0 was used. Two proteins peaks, detected using a UV 280 nm-based detection system, have been collected and neutralized with Tris pH 7.4.

Enzymatic tests can be performed with the recombinant or the native, affinity purified TKTL1 protein.

(C) Detection of Suitable Compounds by Determining the Two-Substrate Transketolase Reaction.

(C-1) The transketolase (two-substrate) activity of TKTL1 was measured by a coupled enzyme assay at 25° C. Reactions were started by addition of recombinant and native TKTL1 protein (a) in the presence of the test compound and (b) in the absence of the test compound and determined spectrophotometrically by the rate of reduction of NAD$^+$ in the following reaction sequence: xylulose-5-phosphate (X5P) and ribose-5-phosphate (R5P)>(TKTL1 activity)>glyceraldehyde-3-phosphate, sedoheptulose-7-phosphate>(glyceraldehyde-3-phosphate dehydrogenase activity [GAPDH])>NAD$^+$→NADH+H$^+$, 1,3-phosphoglycerate.

Transketolase two-substrate activity (a) in the presence of the test compound and (b) in the absence of the test compound was determined in the following reaction (final concentrations): 4 mM X5P, 4 mM R5P, 500 μM NAD$^+$, 2 mM MgCl$_2$, 200 μM thiamine PP, 5 μg recombinant TKTL1 protein, or 4 μg native TKTL1 protein, 3 U GAPDH, 0.15 mol/l Tris buffer pH 7.4 in a reaction volume of 1 ml. Transketolase one-substrate activity was determined by omitting R5P, using X5P solely as substrate. GAPDH was obtained from Sigma.

(C-2) Transketolase activity (a) in the presence of the test compound and (b) in the absence of the test compound can be measured by using a conventional enzyme-linked method under conditions in which coupling enzymes are not limiting. Reactions are initiated by the addition of transketolase protein to an otherwise complete reaction mix of 100 mmol/L Tris-HCl (pH 7.5), 10 mmol/L ribose 5-phosphate, 2 mmol/L xylulose 5-phophate, 1.2 mmol/L $MgCl_2$, 0.1 mmol/L NADH, 2000 U/L glycerol-3-phosphate dehydrogenase and triose phophate isomerase. Reactions are conducted at 37° C. The oxidation of NADH, which is directly proportional to transketolase activity, is followed by monitoring the decrease in absorbance at 340 nm.

(C-3) Substrates (in variable concentrations) can be tested as possible donors if erythrose-4-phosphate (1 mM) as acceptor is used. In such a reaction fructose-6-phosphate will be build. With the enzymes glucose-6-phosphate-dehydrogenase and 6-phosphoglucose-isomerase, fructose-6-phosphate will be oxidized to 6-phosphogluconolactone, leading to the generation of NADPH.

(C-4) Formaldehyde (variable concentrations) as acceptor can be used leading to dihydroxyacetone. The following reaction of glycerin-dehydrogenase builds glycerin, concomitant with an oxidation of NADH.

(D) Determining the One-Substrate Transketolase Reaction (D-1) via oxidation of NADH:

Transketolase activity (a) in the presence of the test compound and (b) in the absence of the test compound is measured by using a conventional enzyme-linked method under conditions in which coupling enzymes are not limiting. Reactions are initiated by the addition of transketolase protein (a) together with the test compound and (b) in the absence of the test compound to an otherwise complete reaction mix of 100 mmol/L Tris-HCl (pH 7.5), 5 mmol/L xylulose 5 phophate, 1.2 mmol/L $MgCl_2$, 3 mmol/L phosphate, 0.1 mmol/L NADH, 2000 U/L glycerol-3-phosphate dehydrogenase and triose phophate isomerase. Reactions are conducted at 37° C. The oxidation of NADH, which is directly proportional to transketolase activity, is followed by monitoring the decrease in absorbance at 340.

(D-2) via reduction of NAD:

Transketolase activity (a) in the presence of the test compound and (b) in the absence of the test compound is measured by using a conventional enzyme-linked method under conditions in which coupling enzymes are not limiting. Reactions are initiated by the addition of transketolase protein (a) together with the test compound and (b) in the absence of the test compound to an otherwise complete reaction mix of 100 mmol/L Tris-HCl (pH 7.5), 5 mmol/L xylulose 5 phophate, 3 mmol/L phosphate, 1.2 mmol/L $MgCl_2$, 0.1 mmol/L NAD, 2000 U/L glyceraldehyde-3-phosphate dehydrogenase. Reactions are conducted at 37° C. The reduction of NAD, which is directly proportional to ketolase activity, is followed by monitoring the increase at 340 nm. In addition, generation of acetyl-phosphate can be measured.

(E) Determining Transketolase Reaction with Further Substrates

Transketolase activity (a) in the presence of the test compound and (b) in the absence of the test compound is measured by using a conventional enzyme-linked method under conditions in which coupling enzymes are not limiting. Reactions are initiated by the addition of transketolase protein (a) together with the test compound and (b) in the absence of the test compound to an otherwise complete reaction mix of 100 mmol/L Tris-Cl (pH 7.5), 5 mmol/L acetaldehyde, 5 mmol/L pyruvate, 12 mmol/L $MgCl_2$. The reaction leads to 3-hydroxybutanon (acetoin) and $CO_2$. Reactions are conducted at 37° C. Transketolase activity is measured by HPLC-chromatography.

Further substrates can be:

(a) Formaldehyde and pyruvate leading to hydroxyaceton and $CO_2$.

(b) Glycerinaldehyde and pyruvate leading to 1-desoxyxylulose and $CO_2$.

(F) In Vivo Assays for Identification of TKTL1 Inhibitors Based on Lactate Production Cell lines, which can be tested are, e.g., glioblastoma cell line LN18, colon cancer cell line HT29, breast cancer cell line MCF7. Cell lines have to be grown in media containing 2 mg/ml glucose (a) in the presence of the test compound and (b) in the absence of the test compound.

Glucose consumption and lactate production has to be determined for 5 days. Every day the glucose and lactate content in the media is tested. As an additional control, glioblastoma cell line LN229 could be used, which does not show high glucose consumption and a high lactate production rate.

Example 10

Screening Methods for Drug Candidates (A) Assays for Single Compound Testing

Cell lines (e.g., as described above) should be grown with and without the compound to be tested. As synthetic test compounds, for example, thiamin, oxythiamin, p-hydroxyphenylpyruvate, pyrithiamin, amprolium, 2-methylthiamin, benfooxytiamine, benfotiamine, 2-methylthiamine, 2-methoxy-p-benzoquinone (2-MBQ), and 2,6-dimethoxy-p-benzoquinone (2,6-DMBQ), genistein, and flavonols as e.g. quercetin, catechins, nitrilosides and anthocyanins or derivatives of them can be used.

Derivatives of the above listed compounds can be generated by substituting or adding one or more of the following groups:

linear and branched ($C_1$-$C_{12}$) aliphatic alkyl groups, substituted with at least one group chosen from OH, $NH_2$, SH, CN, $CF_3$, halogen, $CONHR^5$, $COOR^5$, $OR^5$, $SR^5$, $SiOR^5$, $NHR^5$, aliphatic ($C_3$-$C_6$) rings, and aromatic ($C_3$-$C_6$) rings, wherein $R^5$ is chosen from linear and branched ($C_1$-$C_4$) alkyl groups, aryl groups, natural polymers, synthetic polymers, and copolymers, said polymers and copolymers carrying at least two groups chosen from: hydroxyl, carboxylate, primary amine, secondary amine, tertiary amine, thiol, and aldehyde;

a hydrogen atom, a halogen atom, $CF_3$, OH, $OCF_3$, COOH, $R^7$, $OR_5$, and $OCOR^7$, wherein $R^7$ is chosen from linear and branched ($C_1$-$C_4$) aliphatic alkyl groups;

a monohalogenated and polyhalogenated linear and branched ($C_1$-$C_4$) alkyl groups, and from aryl groups, wherein the aryl groups are optionally substituted with at least one group chosen from OH, $NH_2$, SH, CN, $CF_3$, halogen, COOH, $CONHR^8$, $COOR^8$, $OR^8$, $SR^8$, and $NHR^8$, wherein $R^8$ is chosen from linear and branched ($C_1$-$C_{12}$) alkyl radicals; and from linear and branched ($C_1$-$C_4$) alkyl groups, and a $CF_3$ group.

Natural products, or extracts or fractions thereof can also be used to identify compounds for activating or inhibiting TKTL1 enzymatic activity, e.g., fermented wheat germ extract AVEMAR or apple extracts. Substrates or substrate-analogues specific for TKTL1 can be used to accelerate or inhibit TKTL1 enzymatic activity. Reactions specific for the TKTL1 protein isoforms can be exploited to inhibit or activate TKTL1 enzyme activities. Compounds which inhibit the TKTL1 enzymatic activity can be used to prevent obesity.

Thus, compounds can be identified which will lead to a reduced glucose consumption or lactate production. Such compounds are, e.g., useful for reducing obesity, for reducing or inhibiting spermatogenesis, lactate production in sperms (leading to a matrix degradation in uterus) thus can be applied as contraceptives.

Moreover, compounds can be identified which will lead to an enhanced glucose consumption or lactate production. Such compounds can be used, e.g., for accelerating wound healing and bone repair, for reducing and normalizing blood glucose levels in diabetes mellitus patients, for preventing or reducing pathological alterations in small and large vessels in diabetes mellitus patients, for reducing retinopathies or neuropathies in diabetes mellitus patients and for inhibiting or preventing neurodegenerative diseases like Alzheimer disease, Wernicke-Korsakoff syndrome, Huntington disease, and Morbus Parkinson.

(B) Assays for Determining Compounds Influencing the Protein-Protein Interactions of the Mutated TKTL1 Protein Isoforms Protein-protein interactions play a role both in regulating enzymatic activity and in signal transduction pathways that regulate cellular function. The number of small molecules protein-protein interaction inhibitors (SMPIIs) is growing rapidly. Living cells are continuously exposed to a variety of signals from their micro- and macro-environment. Many of these signals are detected by receptors present on the cell surface, and are then processed and transduced by intracellular signalling cascades. Because the ultimate site of action in a signalling cascade is often far from the cell surface, an inherent feature of intracellular signalling pathways is the requirement that proteins translocate from one position to another within the cell. These translocations, and thus cell signalling and response, depend critically on protein-protein interactions that mediate protein translocation through the intracellular space.

As an example of a typical signal transduction pathway involving protein translocation, the signalling and protein translocation steps involved in the cellular response of the phosphatidylinositol 3 kinase (PI3K) pathway to a growth factor such as insulin is depicted. This pathway influences and is influenced by TKTL1.

1. Insulin binds to and activates its receptor at the cell surface. Upon activation, the receptor recruits adaptor proteins and activates intracellular signalling molecules including PI3K.
2. Activated PI3K increases the plasma membrane concentration of the lipid phosphatidylinositol 3,4,5-triphosphate (PIP3).
3. PIP3 in the plasma membrane provides docking sites for protein kinases including Akt1/PKBa and PDK1; Akt is activated by PDK1 only when both are docked at the membrane. This translocation step is an absolute requirement for Akt activation.
4. Once activated by PDK1 at the plasma membrane, Aid is free to diffuse back into the cell interior, where it can phosphorylate substrate such as the transcription factor Forkhead (FKHR, FOXOA1).
5. Unphosphorylated FKHR normally resides in the nucleus, where it modulates genes involved in cell cycle arrest and apoptosis. However, once phosphorylated by Akt1, FKHR translocates to the cytoplasm, where it can no longer modulate target genes.

Protein-protein interactions and translocations are involved at each of these steps, notably for Aktl and Forkhead. Thus, a signal initiated by the binding of insulin to a cell surface receptor modulates the transcription of genes involved in cellular growth and survival via a sequential cascade of protein translocation events. The therapeutic relevance of this becomes clear when one considers that altered signalling responses are often key distinguishing features between cells in normal and diseased tissues.

(C) Assays for Small-Molecule Protein-Protein Interaction Inhibitors

Historically, large peptides and natural products have been considered the primary compound classes capable of modulating protein-protein interactions. However, there is growing evidence in the literature and from screening initiatives to suggest that small molecules can also modulate the interactions responsible for protein-protein complexes. These compounds may act either directly—via inhibition at the protein-protein interface—or indirectly—via binding to an allosteric site and induction of a conformational change of the target protein or an associated molecule.

Traditional small molecule drug discovery focuses primarily on the activity of compounds against purified targets, such as binding to cell-surface receptors or inhibition of the catalytic activity of enzymes. While these approaches have led to the development of a large number of useful drugs, they clearly have limitations. Because of the complex network environment in which intracellular signalling occurs, it is advantageous to screen compounds in living cells to reproduce the pathway and network context in which the drug will eventually have to act. When employed as part of a pathway screening strategy, cell-based translocation assays offer an opportunity to discover and progress entirely new classes of compounds that act primarily by modulating protein interactions.

Cell-based assays that monitor the intracellular behaviour of target molecules, rather than binding or catalytic activity of purified proteins, can now be used in high-throughput screens to discover and profile SMPPIIs.

Known transketolase (TKT) genes encode a single protein with enzymatic activity, whereas TKTL1 transcripts and proteins different in size have been detected. Furthermore, part of the TKTL1 protein(s) is present in the nucleus of cells. Therefore the one gene/one protein/one function relationship is wrong for the TKTL1 gene. Known transketolases are homodimers of two full length proteins harbouring all typical invariant transketolase amino acid residues. The transketolase-like gene encoded TKTL1 protein isoforms build TKTL1 homo/heterodimers and TKT/TKTL1 (and TKTL2/TKTL1) heterodimers. The expression of TKTL1 protein isoforms—even an enzymatically non-active—influences the enzymatic activity of a TKT protein as part of a TKT/TKTL1 heterodimer. The same is also true for TKTL2/TKTL1 heterodimers. A molecular switch and a proton wire synchronizes the active sites in TKT/TKTL1 heterodimers and TKTL1/TKTL1 homo- and heterodimers.

Another type of protein interaction is present as TKTL1 protein isoforms are part of a multi-protein complex. TKTL1 proteins are bound to transketolase unrelated proteins like GAPDH, DNaseX (DNA acc. No. X90392; protein acc. No. CAA62037), (phosphorylated-) Akt, histone, histone acetylase, actin binding protein, and amyloid precursor protein (APP). The presence or binding of each member of the multi-protein complex changes. The changes are influenced by the translocation of cytoplasmic localized proteins to the nucleus. Once arrived in the nucleus, the former cytosolic proteins do exerts functions different to the function within the cytoplasm. We have detected a translocation of DNaseX from the cytoplasm to the nucleus in apoptotic and tumor cells. We have also detected a translocation of ph-Akt from the cytoplasm to the nucleus in tumor cells (FIG. 6-8). A translocation of GAPDH has been detected in apoptotic neuronal cells. The release from cytoplasmic binding sites or the new synthesis of proteins, which are directly translocated into the nucleus, leads to multi-protein complexes which are inducing apotosis. This apoptosis is the basis for the death of cells, e.g. neurons in brains of patients with neurodegenerative diseases. In tumor cells the sucide molecule DNaseX is present in the nucleus, (but exerts no DNase activity) which would lead to apoptosis and cell death of the tumor cells. Instead, binding to this multi-protein complex leads to inactivation of DNaseX in tumor cells. Therefore apoptosis is blocked. In neurodegenerative diseases DNaseX, GAPDH and TKTL1 lead to apoptosis of cells, cells which should not die. The unwanted apoptosis lead to the severe effects.

Bound proteins in the multi-protein complex were affinity-purified from cell lines using antibodies directed against TKTL1, DNaseX, ph-Akt, and GAPDH. Binding to certain proteins was assessed by ELISA technique, using e.g. the combination of TKTL1 and GAPDH antibodies; the combination of TKTL1 and DNaseX antibodies; the combination of TKTL1 and ph-Akt antibodies; the combination of TKTL1 and TKT antibodies; the combination of TKTL1 and TKTL2 antibodies.

(D) In Vivo High-Throughput Screen to Discover and Profile SMPPIIs for Influencing Protein-Protein Interactions of TKTL1 Protein Isoforms SMPPIIs can be identified which influence the generation of TKTL1 homo/heterodimers and TKT/TKTL1 heterodimers and the interaction to other proteins of the multi-protein complex. SMPPIIs can be identified which influence the generation of TKTL1 protein interactions with such other proteins e.g. DNaseX, GAPDH or amyloid beta peptide (A beta). SMPPIIs can be identified which influence the generation of TKTL1 protein aggregates.

SMPPIIs can be identified which influence the protein-protein interaction with other proteins and the following generation of protein aggregates e.g. GAPDH or amyloid beta peptide (A beta). SMPPIIs can be identified which influence the translocation of TKTL1 protein isoforms e.g. translocation from cytoplasm to nucleus.

The altered substrate specificity and reaction modus of the TKTL1 enzyme can be used for the destruction of cells or tissues with an enhanced TKTL1 enzyme activity. Application of a nontoxic substrate can be applied to patients with enhanced TKTL1 enzyme activity. Cells with an enhanced expression of TKTL1, harbor a gene product (TKTL1 enzyme) which targets the cells for selective killing. Those cells, which show an enhanced TKTL1 enzymatic activity, convert the nontoxic substrate into a toxic drug by rendering the cells sensitive to a nontoxic prodrug or a chemotherapeutic agent, thereby eliminating unwanted cells. This strategy of killing unwanted cells can be e.g. applied for epithelial cell (head and neck, oesophagus, gastric, colon and rectum and urothelial cells) by administering nontoxic prodrugs e.g. in food.

(E) Mutations within the TKTL1 Gene have been Detected Leading to TKTL1 Protein Isoforms with Different Isoelectric Properties and Reduced Affinities for Thiamine:

A test can be performed identifying mutations within the TKTL1 gene by DNA-based methods. A test can be performed by isolating TKTL1 protein isoforms using a monoclonal antibody specific for the TKTL1 protein(s). The antibody could be attached to microtiter plates. Serum or other samples could be analyzed and the TKTL1 protein isoform can be isolated form these specimens. A standardized enzymatic transketolase test could be performed allowing the determination of transketolase activity or Km-values for thiamine. Using this procedure, individuals with reduced TKTL1 activities could be identified prior to the beginning of the disease e.g. diabetes mellitus, Wernicke-Korsakoff syndrome, Huntington disease. Those patients should be treated with a TKTL1 activator compound.

An in vivo assay with cells can be performed for screening small compound inhibiting the translocation to the nucleus or the aggregation of TKTL1 protein within the nucleus, as monitored e.g. by (in vivo) immunohistochemical methods. Cells can be analysed for the presence of high molecular weight complexes harbouring TKTL1 or the presence of protein complexes with reduced solubility. The above mentioned in vivo assays can also be performed using a TKTL1-GFP fusion protein.

Example 11

Controlling of the mam-aGF Via Nutrition Based Therapy

A further embodiment of the invention relates to a novel therapeutic approach which is based on the expression of TKTL1 and its concomitant sugar metabolism. Besides the inhibition of TKTL1 enzymatic activity by small compounds or inhibitory substrates, TKTL1 enzymatic activity can also be inhibited by limited substrate availability through application of a targeted nutrition. The targeted nutrition based therapy or prevention consists of a test for the determination of TKTL1 enzymatic activity in tumors or non malignant cells/tissues followed by a specific nutrition.

The basic nutrition consists of a selected fatty acids composition, preferably in an amount of 55 to 65% (w/w); a selected carbohydrate composition, preferably, in an amount of 5 to 15% (w/w) with, preferably, less than 2% (w/w) glucose (or starch) content, preferably, mainly comprising fructose, oligofructose, galactose, oligogalactose; a selected protein (aminoacid) composition, preferably, in an amount of 10 to 25% (w/w) with, preferably, more than 40% (w/w) (lysine, leucine), and, preferably, more than 30% (w/w) (isoleucine, phenylalanine, threonine, tryptophan, tyrosine); tocotrienol and electron acceptors or combination thereofs:

A preferred embodiment consist:
a) 62% of a combination of fatty acids (see Table 1);
b) 12% carbohydrates with less than 2% glucose (or starch) content, mainly consisting of fructose, oligofructose, galactose, oligogalactose;
c) 18% proteins with more than 40% (lysine, leucine), and more than 30% (isoleucine, phenylalanine, threonine, tryptophan, tyrosine)
d) Tocotrienol (e.g. gamma-tocotrienol)
e) at least one electron acceptor, such as, for example, parabenzoquinones, benzoquinones, hydroxyquinones and derivates thereof.

The basic nutrition in combination with a pharmaceutically acceptable carrier and thiamin or thiamin derivates (etc. benfotiamine) which are activating the TKTL1 enzymatic activity will be applied to prevent or treat neurodegenerative diseases, diabetes, diabetes complications, metabolic syndrome, macro- and microvascular damages, aging, retinal cell damage, central, inflammation of endothelial cells, and peripheral neuronal cell damage, because in normal (not malignant) cells like, for example, retina cells, central and peripheral neurons, and endothelial cells, the TKTL1 activity protects from damaging effects of insufficient sugar metabolism leading to AGE or radical formation.

For cancer treatment the daily basic nutrition has to be adjusted, preferably, to a maximal total amount of 0.2 mg thiamine. This can be done by selection of nutrition with low thiamine level, by thiaminase treatment of nutrition or by heating/boiling of nutrition. The basic nutrition with a pharmaceutically acceptable carrier and low levels of thiamine or the basic nutrition with low levels of thiamine supplemented with inhibitory thiamine analogs (etc. oxythiamin, oxybenfotiamine) is administered to cancer patients, if a high TKTL1-activity and/or transcript/protein concentration in their tumors or metastases is detected. This nutritional approach leads to an inhibition of TKTL1 enzymatic, thereby reducing glucose metabolism and inhibiting tumor proliferation.

TABLE 1

Example of a fatty acid mixture in weight %:

| | |
|---|---|
| caprylic acid (C8) | 46.6 |
| capric acid (C10) | 28.2 |
| linoleic acid (ω6-C18:2) | 3.6 |
| SDA (ω3-C18:4) | 0.2 |
| ETA (ω3-C20:4) | 0.3 |
| EPA (ω3-C20:5) | 5.7 |
| DPA (ω3-C22:5) | 0.9 |
| DHA (ω3-C22:6) | 4.9 |
| other | 9.6 |
| total MCFA's | 74.8 |
| total n-3 PUFA's | 12.0 |
| total other | 13.2 |
| DHA:EPA | 0.86 |
| n-3:n-6 | 3.1 |

MCFA = Medium chain fatty acids, i.e. fatty acids having 8-14 carbon atoms),
PUFA = Polyunsaturated Fatty Acids, i.e. fatty acids having more than one double bond)

Example 12

Detecting of the TKTL1-Protein-Level in Cancer Tissue and in Normal (Healthy) Tissue of Thyroidea, Lung and Colon Five µm thick human cancer and normal paraffin sections of thyroid tissue, lung tissue and colon tissue were analyzed by immunohistochemistry. Dewaxed sections were heated for antigen unmasking in 10 mM sodium citrate (pH 6.0) for 1 minute at 450 W followed by 5 minutes at 100 W. After rinse in $dH_2O$, inhibition of endogenous peroxidase was performed with 5 min incubation with $3\%-H_2O_2$. Then, sections were exposed to biotin blocking system (DAKO) for 10 min to block endogenous avidin-biotin. After two washes in Tris/saline buffer (TBS), slides were incubated with 1% goat serum for 30 min to block unspecific staining. Successively, sections were exposed to mouse anti-TKTL1 (clone JFC12T10; mouse $IgG2_b$) antibody (25 µg/ml) or anti-Ser473 phospho-Akt (587F11; mouse $IgG2_b$; Cell Signaling Technology) overnight at 4° C. Then slides were washed in TBS and incubated with biotinilated anti-mouse immunoglobulins for 30 min at room temperature and treated with streptavidin-peroxidase (DAKO). Staining was revealed using 3-amino-9-ethylcarbazole (AEC) substrate. Nuclei counterstaining was performed using aqueous haematoxylin.

The results of that immunohistochemical staining are shown in FIGS. 6, 7 and 8. For each cancer type one representative of three independent experiments is shown. TKTL1 and phosphorylated Akt are highly expressed in thyroid cancer tissue. Non small lung cancer (NSLC) and colon carcinomas express high levels of TKTL1 and phosphorylated Akt.

Example 13

Detecting of the TKTL1-Protein-Level in Tumors of Gastric Carcinoma Patients, Colon Carcinoma Patient and Noninvasive and Invasive Bladder Carcinoma Patients The TKTL1 protein expression in tumors of three gastric carcinoma patients (FIG. 4 A-P), one colon carcinoma patient (FIG. 4 Q), one noninvasive bladder carcinoma patient (FIG. 4 R) and one invasive bladder carcinoma patient (FIG. 4 S-T) was determined and compared with corresponding normal tissue.

TKTL1 protein determination was carried out by help of a monoclonal anti-TKTL1 antibody. The anti-TKTL1 antibody was revealed by diaminobenzidine tetrahydrochloride (DAB; brown staining). Counterstaining was performed with haematoxylin (blue staining).

The specimens of gastric carcinoma patient 1 reveal strong cytoplasmic expression of TKTL1 in tumor tissue but no expression in the surrounding stroma cells (FIG. 4 C-F). Note the heterogenous expression in tumor cells (FIG. 4 E-F) The corresponding normal tissue shows no expression of TKTL1 (FIG. 4 A-B).

The specimens of gastric carcinoma patient 2 reveal strong cytoplasmic expression within tumor cells (FIG. 4 J-N) and heterogenous expression in tumor cells (FIG. 4 L). The corresponding normal antrum tissue shows no expression of TKTL1 (FIG. 4 G-I).

The specimens of gastric carcinoma patient 3 reveal nuclear expression in a poorly differentiated gastric carcinoma (FIG. 4 O-P).

The specimens of colon carcinoma patient reveals cytoplasmic staining (FIG. 4 Q).

The specimens of the patient with superficial bladder carcinoma reveals no expression of TKTL1 (FIG. 4 R).

The specimens of the patient with an invasive poorly differentiated bladder carcinoma reveals strong cytoplasmic expression (FIG. 4 S-T).

A comparison of noninvasive and invasive bladder carcinoma tissue is shown in FIG. 5. The non-invasive bladder carcinoma tissue shows non or only few staining which indicates no expression of TKTL1 while the invasive bladder carcinoma tissue shows strong staining that indicates strong expression of TKTL1.

Example 14

Expression of TKTL1 Protein Isoforms in Five Tumor Cell Lines Derived from Four Different Tumor Entities The expression of TKTL1 protein isoforms in five tumor cell lines derived from four different tumor entities were detected using a MAb specifically detecting TKTL1 protein isoforms and not reacting with other transketolase family members. The results are shown in FIG. 2 (B). Each cell line do show a unique expression pattern of TKTL1 protein isoforms. The molecular weight standard is indicated in kDa.

Example 15

Expression of TKTL1 and Phosphorylated Akt (pH-Akt) in Cancer and Normal Tissue Immunohistochemical analysis of TKTL1 or ph-Akt was carried out on paraffin-embedded sections of normal, papillary (PTC), follicular (FTC), and undifferentiated (UTC) thyroid cancer (FIG. 6 A-C), of normal and NSLC tissues (FIG. 7 D), of colon cancer (FIG. 7 E) and of normal or bladder and prostate cancer (FIG. 8 F-G) with Anti-TKTL1 or anti-ph-Akt. Anti-TKTL1 or anti-ph-Akt was revealed by 3-amino-9-ethylcarbazole (AEC; red staining). Counterstaining was performed with haematoxylin (blue staining). Negative controls were performed using isotype matched IgG.

TKTL1 is mainly localized within the cytoplasm, but a nuclear staining can also be identified in a subset of tumors. Phosphorylated Akt is localized within the cytoplasm and/or the nucleus.

Example 16

Detecting of the TKTL1-Level in Patients with Gastric Carcinoma, Patients with Colon Carcinoma, Patients with Noninvasive Bladder Carcinoma and Patients with Invasive Bladder Carcinoma Three µm thick paraffin sections were heated for antigen unmasking in 10 mM sodium citrate (pH 6.0) for 5 minutes at 900 W, for 5 min at 900 W in dH$_2$O, and for 5 min in 10 mM sodium citrate (pH 6.0) at 900 W. After a wash in phosphate/saline buffer (PBS), inhibition of endogenous peroxidase was performed as above described. Then, sections were exposed 15 min to biotin-avidin blocking buffer (Vector Laboratories). Blocking of unspecific staining was performed with goat serum as described above. Primary antibodies were visualized with avidin-biotinylated horseradish peroxidase complex (ABC) and diaminobenzidine tetrahydrochloride (DAB) (Elite kit; Vector Laboratories), and counterstained with Mayer's haematoxylin.

The results of the immunohistochemical stainings are shown in FIGS. 4, 5, and 9-16.

Example 17

Quantification of TKTL1 Transcripts in Gastric and Lung Adenocarcinoma Samples and their Corresponding Normal Tissues 15 µl of the real-time PCR reaction was loaded onto a 3%-agarose gel to visualize the 150 by TKTL1 amplification product. Expression differences between tumor and corresponding normal tissue have been calculated on basis of the real-time data and are shown as fold-induction in tumor sample relative to the corresponding normal sample. (B) Real-time transcript quantification of TKT, TKTL1, TKTL2, and β-actin gene in a lung adenocarcinoma and corresponding normal sample. The highest expression level is observed for the β-actin. Within the transketolase gene family, the TKT gene shows the highest expression level. The TKTL1 and TKTL2 expression level in normal lung is low compared to that of TKT and β-actin. In contrast to this, the expression level of TKTL1 in lung adenocarcinoma is 60-fold higher than in the corresponding normal tissue.

Example 18

Diagnosis of Neurodegenerative Diseases

Fibroblast cell lines, foreskin fibroblasts or leukocytes from healthy subjects and patient with Alzheimer's disease, or other neurodegenerative diseases were analyzed for TKTL1 abnormalities by means of ELISA, electrofocusing gel analysis, 2D-gel electrophoresis and immunostaining. The ELISA experiments were performed by different ELISA approaches. One type of ELISA represents a typical ELISA, where catching or detecting antibody is directed against a certain protein. The other type of ELISA used consisted of an antibody directed against one protein and an antibody against another protein. An example for type 1 ELISA is the combination of TKTL1 antibody JFC12T10 and TKTL1 antibody JFC10T9. JFC12T10 detects an epitop of the TKTL1 protein, and does not cross react with TKT or TKTL2. JFC10T9 detects another epitop of TKTL1. Using the ELISA JFC12T10/JFC10T9 TKTL1 protein can be detected and measured. An example for Type 2 ELISA is antibody JFC12T10 directed against TKTL1 and antibody JFC11D8 directed against DNaseX. Using this ELISA the protein interaction of TKTL1 and DNaseX can be determined. Both types of ELISA reactions were performed with samples from healthy persons and patients. One type of sample consisted of body fluids like serum and was directly analysed for the presence of proteins and protein interactions. Another type of analysis was performed using an antibody (e.g. JFC12T10 or JFC11D8) coupled to carbolink. Using affinity purification procedures we isolated multi-protein complexes of cells (derived from cell culture or native tissues). The multi-protein complexes were analysed by electrofocusing or 2D-gel electrophoresis followed by immunostaining or determination of enzymatic activity (e.g. transketolase two- or one-substrate reaction; DNase test, GAPDH activity). Using these assays, protein isoforms could be identified specifically present in patients with neurodegenerative diseases like AD. In patients with neurodegenerative disorders like AD patients, TKTL1 variants have been detected with high alkaline pI, lower two- or one-substrate reaction, and lower thiamin affinity. Additionally, using standard PAGE smaller protein isoforms and a higher amount of smaller protein in comparison to full length TKTL1 were detected in intact cells or cell extracts from those patients compared to healthy persons. Furthermore reduced two- or one-substrate reaction of TKTL1, or lower thiamin affinity of TKTL1 has been observed in healthy persons which later on (month and years later) showed neurodegenerative disease like AD. The observed TKTL1 variants lead to reduced sugar metabolism in cells. These reduced sugar metabolism lead to enhanced AGE formation and AGE formation lead to high molecular protein aggregates and cell death. This unwanted cell death of cells necessary for proper brain function, is an important cause for these neurodegenerative diseases. To identify individuals which do have TKTL1 variants with a reduced two- or one-substrate reaction or lower thiamin affinity, TKTL1 antibodies were established, which can be used to isolate TKTL1 proteins from samples to be tested (e.g. JFC12T10). Those samples can be body fluids (e.g. serum) or cell samples (e.g. proteins of fibroblasts or leukocytes). TKTL1 antibodies coupled to ELISA plates catch the TKTL1 proteins and after washing away TKT and TKTL2 proteins, the (trans-)ketolase two- or one substrate reaction can be enzymatically determined in a coupled enzymatic reaction by e.g. building the reduced NADH (the enzymatic assays are described above). Similarly the enzymatic reaction was performed at different concentrations of thiamin. By reducing the thiamine level in the assay TKTL1 variants were identified in patients with neurodegenerative diseases with a reduced affinity for thiamine. Using this approach of ELISA and enzymatic analysis, TKTL1 variants can be identified which predispose to neurodegenerative diseases at a time point before signs of neurodegenerative diseases are present. This can be exploited for a prevention of neurodegenerative diseases e.g. by application of better soluble thiamine derivates like benfotiamine or a diet with reduced levels or certain types of sugars (e.g. glucose). In addition to the identification of TKTL1 variants with a reduced two- or one-substrate reaction or lower thiamin affinity, TKTL1 variants with a reduced solubility or TKTL1 variants present in high molecular weight complexes were identified in neurodegenerative disease patients like AD. The inventors established TKTL1 specific antibodies specifically reacting with TKTL1 variants present in high molecular weight complexes in nuclei of patients with neurodegenerative disease patients like AD (JFC7T4). Using ELISA reactions or immunohistochemical stainings, those disease specific TKTL1 variants can be identified in body fluids (e.g. serum), or in tissue samples (e.g. leukocytes, fibroblasts, biopsies). Furthermore in combination with antibodies directed against other proteins present in those multi-protein complexes, ELISA can be performed detecting the presence of protein interactions. Such an type 2 ELISA consisting of TKTL1 antibody JFC8T7 and DNaseX antibody JFC7D4 identified a protein interaction of TKTL1 and DNaseX, specific for cells going into apoptosis. Another type 2 ELISA consisting of TKTL1 antibody JFC8T7 and GAPDH antibody JFC3G6 identified a protein interaction of TKTL1 and GAPDH, specific for cells going into apoptosis. The presence of these protein complexes can be exploited for the detection and therapy of neurodegenerative diseases. The identification of such protein interactions between TKTL1 and other proteins like GAPDH, DNaseX, and ph-Akt can be exploited for the isolation of antiapoptotic compounds. Those compounds can be used as pharmaceutical agents for the treatment of neurodegenerative diseases. Compounds specifically binding to TKTL1 can be identified by affinity labeling, and e.g. by means of BIAcore technology. Antiapoptotic effect can be detected using reduced programmed cell death (visualized by e.g. apoptotic ladder, caspase-3, annexin). TKTL1 and GAPDH are tightly bound to each other. The TKTL1 (trans-)ketolase reaction cleaving sugars like X5P leads to the production of GAP. As GAPDH is tightly bound to TKTL1, the produced GAP is directly used from GAPDH which lead to the production 1,3-phosphoglycerate concomitant with the reduction of $NAD^+$ to $NADH+H^+$. For the isolation of small compounds inhibiting TKTL1 and GAPDH interactions different $NAD^+$ concentrations should be used since the binding of some compounds is depend on the concentration of $NAD^+$. Another type of protein interaction was detected using antibody JFC12T10 as sole antibody. If the TKTL1 protein is present as a single protein, no ELISA reaction should work if just one antibody is used as catching and detecting antibody. In case of TKTL1 antibody IFC12T10 can be used as catching and detecting antibody. Therefore, using this antibody protein interactions of TKTL1 and another TKTL1 protein can be detected. As some of the TKTL1 protein isoforms miss N-terminal protein sequences dimers consisting of TKTL1 and TKTL1 can be discriminated into homo- and hetero TKTL1-dimers. Some of the dimers consists of full length TKTL1 protein bound to another full length TKTL1 protein (TKTL1 homodimer). Some of the dimers consists of a full length TKTL1 protein and a smaller TKTL1 isoform, where the N-terminus is missing. The discrimination can be performed using TKTL1 antibodies located at different sites within the TKTL1 protein. E.g. N-terminal located TKTL1 antibodies can be used with C-terminal located antibodies and the result of this ELISA can be compared with an ELISA using only C-terminally located antibodies. The ratio between those two ELISA results can be used for the identification of patients and for the identification of healthy persons which will later on get a TKTL1-associacted disease. (See also FIG. 11-12)

Example 19

Expression of TKTL1 in Cendothelial Cells

Figure 9:

The majority of normal tissues and cells do show no expression of TKTL1. In the retina, in endothelial cells and in neuronal cells an expression of TKTL1 is present. Retina, endothelial cells and neuronal cells get damaged by high glucose levels. As shown in FIG. 9 and FIG. 10 TKTL1 protein is expressed in the nucleus and/or the cytoplasm of endothelial cells (and retina, and neuronal cells; not shown).

The invention claimed is:

1. A method for controlling the mammalian aerobic glucose fermentation metabolic pathway comprising: administering to a mammalian individual in need of such controlling an amount of at least one inhibitor of an activity or concentration of human enzyme TKTL 1 effective to control the mammalian aerobic glucose fermentation metabolic pathway, wherein the individual suffers from a disease associated with an enhanced mammalian aerobic glucose fermentation metabolic pathway and wherein said controlling inhibits the mammalian aerobic glucose fermentation metabolic pathway, wherein the inhibitor is selected from the group consisting of oxythiamine, benfooxytiamine, hydroxypyruvate, pyruvate, p-hydroxyphenylpyruvate, pyrithiamin, amprolium, 2-methylthiamine, 2-methoxy-p-benzoquinone (2-MBQ), and 2,6-dimethoxy-p-benzoquinone (2,6-DMBQ); and derivatives thereof.

2. The method of claim 1, wherein the individual suffers from a disease associated with an overexpression of a TKTL-1 gene.

3. The method according to claim 1, wherein said inhibitor is benfooxytiamine or a derivative thereof.

4. The method of claim 1, wherein the individual suffers from cancer associated with an overexpression of TKTL-1 gene in tumor cells.

5. The method of claim 1, wherein said inhibitor is benfooxytiamine.

6. The method of claim 1, wherein the inhibitor is administered as part of a nutrition composition or dietary supplement.

* * * * *